United States Patent
Richardson-Burns et al.

(10) Patent No.: US 9,890,467 B2
(45) Date of Patent: Feb. 13, 2018

(54) IMPLANTABLE ELECTRODE COMPRISING A CONDUCTIVE POLYMERIC COATING

(71) Applicant: Biotectix, LLC, Ann Arbor, MI (US)

(72) Inventors: Sarah Richardson-Burns, Ann Arbor, MI (US); Jeffrey Hendricks, Ann Arbor, MI (US)

(73) Assignee: Biotectix LLC, Ann Arbor, MI (US)

( * ) Notice: Subject to any disclaimer, the term of this patent is extended or adjusted under 35 U.S.C. 154(b) by 126 days.

(21) Appl. No.: 14/212,689

(22) Filed: Mar. 14, 2014

(65) Prior Publication Data

US 2014/0277318 A1 Sep. 18, 2014

Related U.S. Application Data

(60) Provisional application No. 61/794,058, filed on Mar. 15, 2013.

(51) Int. Cl.

| | |
|---|---|
| *A61N 1/05* | (2006.01) |
| *C25D 13/12* | (2006.01) |
| *C25D 13/20* | (2006.01) |
| *C25D 13/22* | (2006.01) |
| *C08L 53/02* | (2006.01) |
| *C09D 5/44* | (2006.01) |

(52) U.S. Cl.
CPC ............ *C25D 13/22* (2013.01); *C08L 53/025* (2013.01); *C09D 5/4407* (2013.01); *C25D 13/12* (2013.01); *C25D 13/20* (2013.01); *A61N 1/05* (2013.01); *C08G 2261/3223* (2013.01)

(58) Field of Classification Search
CPC ........ C25D 13/12; C25D 13/20; C25D 13/22; C08L 53/025; C09D 5/4407; A61N 1/05; C08G 2261/3223
See application file for complete search history.

(56) References Cited

U.S. PATENT DOCUMENTS

| | | |
|---|---|---|
| 5,507,977 A | 4/1996 | Virtanen et al. |
| 5,508,348 A | 4/1996 | Ruckenstein et al. |
| 5,840,387 A | 11/1998 | Berlowitz-Tarrant et al. |
| 5,972,499 A | 10/1999 | Rodriguez et al. |
| 6,099,757 A | 8/2000 | Kulkarni |
| 7,887,830 B2 | 2/2011 | Lindquist et al. |
| 7,899,552 B2 | 3/2011 | Atanasoska et al. |
| 7,908,016 B2 | 3/2011 | Atanasoska et al. |
| 8,005,526 B2 | 8/2011 | Martin et al. |
| 2006/0013849 A1* | 1/2006 | Strickler ............... A61L 29/041 424/422 |

(Continued)

FOREIGN PATENT DOCUMENTS

| | | |
|---|---|---|
| EP | 2 014 718 A1 | 1/2009 |
| WO | 2009/059085 A2 | 5/2001 |
| WO | 2012/059215 A1 | 5/2012 |

OTHER PUBLICATIONS

Barra, G.M.O., et al., "Processing, Characterization and Properties of Conducting Polyaniline-Sulfonated SEBS Block Copolymers," 2004, Euro Poly J, 40:2017-2026.

(Continued)

*Primary Examiner* — Ciel P Thomas
(74) *Attorney, Agent, or Firm* — Senniger Powers LLP

(57) ABSTRACT

The present invention generally relates to coated electrodes comprising an electrically conductive substrate and a polymeric coating, and to methods for the preparation of the same.

35 Claims, 5 Drawing Sheets

(56) References Cited

U.S. PATENT DOCUMENTS

| | | | |
|---|---|---|---|
| 2007/0021569 A1* | 1/2007 | Willis | B01D 71/80 |
| | | | 525/314 |
| 2007/0096066 A1* | 5/2007 | Yoshida | H01B 1/127 |
| | | | 252/511 |
| 2007/0239256 A1 | 10/2007 | Weber et al. | |
| 2007/0278453 A1 | 12/2007 | Zahn et al. | |
| 2009/0242842 A1 | 10/2009 | Suh et al. | |
| 2009/0297909 A1 | 12/2009 | Yamamoto et al. | |
| 2010/0256720 A1 | 10/2010 | Overstreet et al. | |
| 2010/0298514 A1 | 11/2010 | Willis et al. | |
| 2011/0021899 A1 | 1/2011 | Arps et al. | |
| 2011/0033651 A1 | 2/2011 | Yoshida et al. | |
| 2011/0275980 A1 | 11/2011 | Weber et al. | |
| 2012/0208086 A1 | 8/2012 | Plieth et al. | |

OTHER PUBLICATIONS

Bhavani, P., et al., "Characterization of Proton Exchange Membranes Based on SPSEBS/SPSU Blends," 2012, J of Poly Res, 2012, 19:1-10, Article No. 9824.

Chen, S., et al., "Preparation of Size Controllable Polypyrrole Sub-Microcapsules Using SEBS Copolymer as the Building Block," 2006, Macromol Rapid Commun, 27:328-332.

Choi, J-H., et al., Micellar Morphology in Sulfonated Pentablock Copolymer Solutions, 2010, Ind Eng Chem Res, 49:12093-12097.

Elabd, Y.A., et al., "Triblock Copolymer Ionomer Membranes Part I. Methanol and Proton Transport," 2003, J. Membrane Sci, 217:227-242.

Ju, Y-W., et al., "Electrochemical Characteristics of Poly(3-Methyl Thiophene)/Sulfonated-SEBS Composite Electrode for Polymer Battery," 2007, Synthetic Metals, 157:823-826.

Ju, Y-W., et al., "Electrochemical Properties of Polypyrrole/ Sulfonated SEBS Composite Nanofibers Prepared by Electrospinning," 2007, Electrochimica Acta, 52:4841-4847.

Kim, T. Y., et al., "Preparation and Characterization of Poly(3,4-ethylenedioxythiophene) (PEDOT) Using Partially Sulfonated Poly(styrene-butadiene-styrene) Triblock Copolymer as a Polyelectrolyte," 2009, Current Applied Physics, 9:120-125.

Lee, E.S., et al., "In situ Formed Processable Polypyrrole Nanoparticle/Amphiphilic Elastomer Composites and Their Properties," 2004, Polym Int, 53:400-405.

Wang, X-L., et al., "Electro-Active Artificial Muscle Based on Irradiation-Crosslinked Sulfonated Poly(Styrene-Ran-Ethylene)," 2010, Sensors and Actuators B, 145:635-642.

Sulfonated Styrenic Pentablock Copolymer Membranes, Kraton-General, 33 pages.

International Search Report issued for PCT/US2014/028380, dated Jul. 28, 2014, 5 pages.

International Search Report issued for PCT/US2014/038630, dated Sep. 17, 2014, 6 pages.

* cited by examiner

IMPLANTABLE ELECTRODE COMPRISING A CONDUCTIVE POLYMERIC COATING

CROSS-REFERENCE TO RELATED APPLICATIONS

This application claims the benefit of U.S. Provisional Patent Application Ser. No. 61/794,058, filed Mar. 15, 2013, the entirety of which is herein incorporated by reference.

FIELD OF THE INVENTION

The present invention generally relates to coated electrodes comprising an electrically conductive substrate and a polymeric coating, and to methods for the preparation of the same.

BACKGROUND OF THE INVENTION

Biomedical electrodes are a primary component of many medical devices, including cardiac pacemakers and defibrillators, deep brain stimulation devices, cochlear implants, peripheral nerve stimulation devices, spinal cord stimulation devices for pain management, and diagnostic tools. The electrode(s) found on the tip of biomedical leads are placed in contact with the appropriate target tissue, and are used to transmit bio-electrical signals to and from the device and target tissue.

A variety of implantable medical devices on the market today utilize conductive electrode coatings comprised of metal oxides or metal nitrides. Depending on how they are deposited, coatings comprised of metal oxides or metal nitrides can have a variety of topographies and morphologies. When used for medical device electrode coatings, metal oxides or metal nitrides are typically formulated with a microscale roughness and/or porosity such that the surface area is significantly increased over that of the uncoated electrode, which lowers the overall electrical impedance. Despite their rough, high surface area topography, however, metal oxide and metal nitride coatings are still mechanically hard compared to the surrounding soft, biological tissue, which is undesirable in the context of a medical device, and particularly a device intended for long-term implantation.

Furthermore, when used with devices that deliver electrostimulation therapies, common metal oxide electrode coatings become increasingly destabilized as the electrode undergoes cycles of biphasic pulse stimulation, due to the build-up of brittle oxide layers at the surface of the electrode. This degradation of the coating presents numerous problems and undesirable qualities for implanted medical device electrodes; these are the potential for tissue injury due to exposure to the delaminated chunks/layers of metal oxide and exposure to potentially harmful non-uniform or higher than usual charge densities caused by the resulting non-uniform electrode surface.

Conductive polymer coatings have the potential to overcome some of the drawbacks associated with traditional metal oxide or metal nitride coatings. For example, conductive polymer coatings derived from poly(3,4-ethylenedioxythiophene) (PEDOT) have been widely used in the electronics industry. Many of the PEDOT-based coatings used in the prior art, however, have limited utility for biomedical leads/electrodes because the processes for applying the coating are broad and non-specific. Even with extensive masking, a cast, dipped, sprayed, or chemical vapor deposition (CVD)-deposited polymeric film cannot easily be localized to the conductive regions or components of a medical electrode.

In addition, cast, dipped, sprayed, or CVD-deposited coatings of PEDOT-derived coatings on metal substrates often confer limited relative improvement in conductivity when compared to the metal alone, and in some cases, the polymeric film can even be insulating, due to a dispersion of leftover solvent throughout the coating. Furthermore because these coating methods apply the PEDOT-derived coating when it is already in a polymeric form, there is little opportunity for electrostatic bond formation and dipole alignment between the PEDOT polymer and underlying metal substrate during the deposition process. As a result, cast, dipped, and sprayed PEDOT-derived coatings typically exhibit limited adhesion to metal substrates.

It is therefore desirable to develop a conductive electrode coating that exhibits greater mechanical, chemical, and electrical stability than the coatings known in the art, that provides excellent electrical conductivity, and that is biologically acceptable for use in medical device applications.

SUMMARY OF THE INVENTION

The present invention is generally directed to a coated electrode comprising an electrically conductive substrate and a polymeric coating, wherein the polymeric coating comprises a reaction product of a polymerization mixture comprising: (a) a conductive monomer or a conductive polymer; and (b) a polyanionic counterion component comprising a block copolymer having the structure of formula (1), (2), (3), or (4):

  (1)

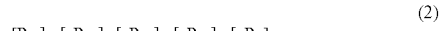  (2)

  (3)

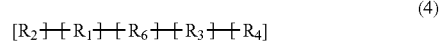  (4)

wherein $R_1$, $R_3$, and $R_5$ independently comprise a high glass transition temperature (high $T_g$) polymer having a $T_g$ greater than 50° C. and less than the melting temperature ($T_m$) of the polymer, and having an average number of repeat units of from about 15 to about 300; $R_2$, $R_4$, and $R_6$ independently comprise a low glass transition temperature (low $T_g$) polymer having a $T_g$ less than 30° C., and having an average number of repeat units of from about 200 to about 5000; and from about 10 to about 100 mol % of repeat units of the high $T_g$ polymer in $R_1$, $R_3$ and $R_5$ are functionalized with a negatively charged functional group, and/or from about 10 to 100 mole percent of repeat units of the low $T_g$ polymer $R_2$, $R_4$, and $R_6$ are functionalized with a negatively charged functional group.

In another aspect, the present invention is generally directed to a coated electrode comprising an electrically conductive substrate and a polymeric coating, wherein the polymeric coating comprises a reaction product of a polymerization mixture comprising: (1) a conductive monomer or a conductive polymer; and (2) a polyanionic counterion component comprising a block copolymer. The block copolymer comprises: (a) two or more styrenic blocks independently comprise polystyrene, poly(t-butyl styrene), polymethyl styrene, poly amino styrene, poly carboxylic acid styrene, or a mixture and copolymer thereof; and (b) one or more elastomeric blocks independently comprise polyethylene, polybutylene, polybutadiene, polyisoprene, polyisobutylene, or a mixture or copolymer thereof. From about 10 to 100 mole percent of the repeat units of the two or more styrenic blocks are functionalized with a negatively charged functional group.

A further aspect of the present invention is generally directed to a coated electrode comprising an electrically conductive substrate and a polymeric coating, wherein the polymeric coating comprises a reaction product of a polymerization mixture comprising: (1) a conductive monomer or a conductive polymer; and (2) a polyanionic counterion component comprising a random copolymer. The random copolymer comprises: (a) styrenic repeat units comprising styrene, t-butyl styrene, methyl styrene, a carboxylic acid-functionalized styrene, an amine-functionalized styrene, or a mixture thereof; and (b) elastomeric repeat units comprising polyethylene, polybutylene, polybutadiene, polyisoprene, polyisobutylene, or a mixture thereof. From about 10 to 100 mole percent of the repeat units are functionalized with a negatively charged functional group.

Another aspect of the present invention is generally directed to a method of preparing the coated electrodes described herein. The method comprises preparing a polymerization mixture comprising (a) a conductive monomer or a conductive polymer and (b) a polyanionic counterion component, and electrochemically polymerizing the polymerization mixture to form a polymeric coating on an electrically conductive substrate.

Another aspect of the present invention is generally directed to a medical device comprising a coated electrode as described herein.

DESCRIPTION OF THE INVENTION

Figure 1:
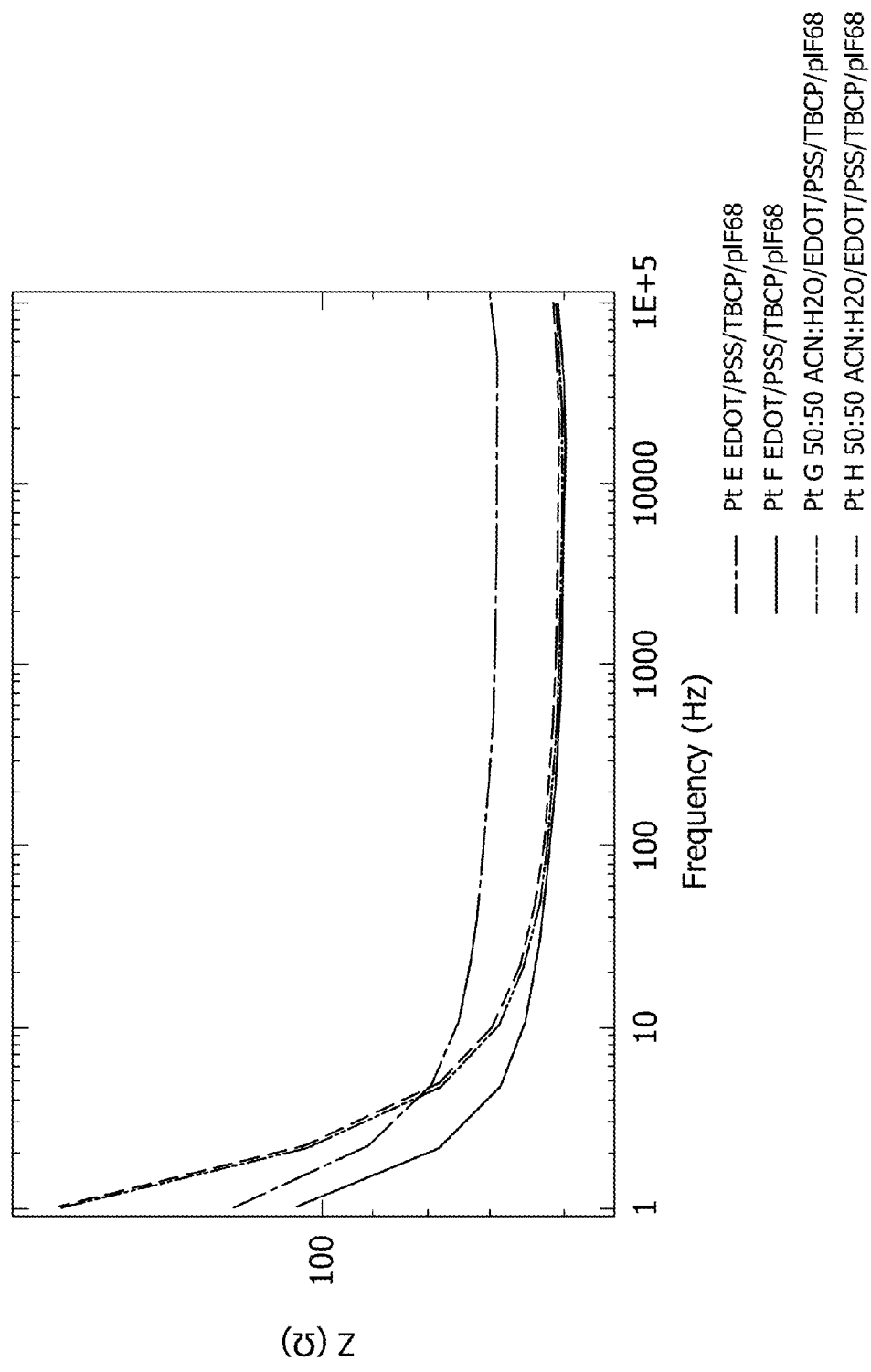
FIG. 1 depicts the results of an impedance spectroscopy test involving the electrodes prepared in Example 4.

It has been discovered that coated electrodes comprising an electrically conductive substrate and a polymeric coating can be prepared having excellent electrical, chemical, and mechanical stability and durability. The coated electrodes disclosed herein address a number of drawbacks exhibited by existing state of the art medical electrode coatings, and provide significant improvements in substrate adhesion, mechanical durability, and electrochemical stability.

The coated electrodes disclosed herein are therefore ideal for use in active implantable medical devices for short-term and long-term implantation in the human body. For example, the polymeric coatings described herein provide the conductive substrate with excellent electrical and charge transfer properties that are ideally suited for interfacing with electrolytes including but not limited to body tissues.

In addition, the polymeric coatings described herein can, in some cases, improve the electrical properties of a conductive substrate to such an extent that the medical device and medical device electrode components can be comprised of less expensive substrate materials (e.g., non-noble metals) than the substrate materials traditionally used for active implantable medical devices.

Due to their ability to improve the electrical properties of a conductive substrate, the polymeric coatings described herein also enable the preparation of medical electrodes, leads, and devices that are smaller, less invasive, and lower profile. The coatings described herein also enable the use of novel device materials and electrode site configurations, spacing, and densities, which collectively make possible the preparation of new medical device materials, designs, geometries, and device delivery methods, including but not limited to devices that are minimally invasive, wireless, leadless, multi-functional, insertable through guide catheters or laproscopes, injectable through syringes or similar insertion devices, or composed of biodegradable or partially biodegradable components.

More particularly, when the coated electrodes described herein are used in medical device applications, they address specific drawbacks of existing and state of the art metal medical device electrodes by providing the metal with significantly improved electrical properties. Specifically, the polymeric coatings described herein can provide a metal medical device electrode with (a) 1 to 3 orders of magnitude decrease in electrode impedance, (b) an increase in charge storage capacity (CSC) often as high as approximately 1000%, and (c) significantly reduced electrode polarization or peak to peak voltage/current response to a biphasic current or voltage pulse. The polymeric coatings described herein therefore can be used to produce medical electrodes having excellent electrical and tissue-interfacing properties that enable better sensing and/or stimulation performance for short-term and long-term medical device applications, as compared to uncoated electrodes or electrodes coated with existing, state of the art coatings.

Generally, therefore, one aspect of the present invention is directed to a coated electrode comprising an electrically conductive substrate and a polymeric coating, wherein the polymeric coating comprises a reaction product of a polymerization mixture comprising (a) a conductive monomer or a conductive polymer, and (b) a polyanionic counterion component.

When synthesizing conducting polymers from monomeric precursors, it is often preferable to introduce counterions that can interact with the conducting polymer molecules, and which can act as dopants to increase the electrical conductivity of the resulting conducting polymer material. The nature of the interaction between conducting polymer and counterion molecules is often electrostatic (e.g., Van der Waals bonds), but in some cases, ionic or covalent bonds can also form between the conducting polymers and the counterion molecules. The coatings disclosed herein generally include a polyanionic counterion component that assists with electrochemical polymerization of the conductive monomer or a conductive polymer, and further can provide the resulting polymeric coating with improved electrical, chemical, and mechanical properties as desired for a particular application.

For example, the polyanionic counterion component typically comprises a block copolymer having the structure of formula (1), (2), (3), or (4):

(1)

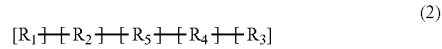

(2)

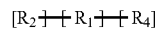

(3)

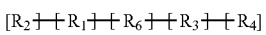

(4)

wherein $R_1$, $R_3$, and $R_5$ independently comprise a high glass transition temperature (high $T_g$) polymer having a $T_g$ greater than 50° C. and less than the melting temperature ($T_m$) of the polymer. Typically, $R_1$, $R_3$, and $R_5$ ("high $T_g$ polymers") each have an average of from about 15 to about 300 repeat units, more typically from about 50 to about 120 repeat units. Blocks $R_2$, $R_4$, and $R_6$ independently comprise a low glass transition temperature (low $T_g$) polymer having a $T_g$ less than 30° C. Typically, $R_2$, $R_4$, and $R_6$ ("low $T_g$ polymers") each have an average of from about 200 to about 5000 repeat units, more typically from about 1000 to about 2000 repeat units.

In the block copolymer of formula (1), (2), (3), or (4) above, from about 10 to 100 mole percent of the repeat units are functionalized with a negatively charged functional group, wherein the mole percentage is based upon the number of repeat units of $R_1$, $R_3$ and $R_5$. For example, typically, from about 10 to 100 mole percent of the units of the high $T_g$ polymer of $R_1$, $R_3$ and $R_5$ are functionalized with a negatively charged functional group. From about 10 to 100 mole percent of the $R_2$, $R_4$, and $R_6$ repeat units can be functionalized with a negatively charged functional group, either in combination with or as an alternative to the functionalization of $R_1$, $R_3$, and $R_5$.

The block copolymer can have the structure of formula (1) or (2). Alternatively, the block copolymer can have the structure of formula (3) or (4).

The high $T_g$ polymer can comprise repeat units derived from a vinyl aromatic monomer. The mole percentage of the repeat units derived from the vinyl aromatic monomer in the high $T_g$ polymer is typically from about 10 to 100 mole percent.

The negatively charged functional group can be a phosphate group, a phosphonate group, a sulfamate group, a carboxylate group, a sulfate group, a sulfonate group, or a combination thereof.

Further, the negatively charged functional group can be selected from the group consisting of a phosphate group, a carboxylate group, a sulfate group, a sulfonate group, or a combination thereof. Typically, the negatively charged functional group is selected from the group consisting of a sulfonate group, a carboxylate group, or a combination thereof. More typically, the negatively charged functional group comprises a sulfonate group.

The negatively charged functional group can comprise a counterion. The counterion can be a proton, an ammonium ion, an organic cation, an alkali metal cation, or an alkaline earth metal cation. For example, the counterion can be sodium, potassium, calcium, magnesium, ammonium, or a combination thereof.

The sulfonate group can comprise a counterion. For example, the sulfonate group can comprise a sodium counterion.

In a typical embodiment, from about 50% to about 70% of the repeat units of the high $T_g$ polymer or the repeat units derived from the vinyl aromatic monomer in $R_1$, $R_3$ and $R_5$ are sulfonated. More typically, from about 55% to about 65% of the repeat units of the high $T_g$ polymer or the repeat units derived from the vinyl aromatic monomer in $R_1$, $R_3$ and $R_5$ are sulfonated.

As described in further detail below, the coated electrode typically comprises a polymeric coating that has been applied to the conductive substrate by electrodeposition. More typically, the polymeric coating is formed over the conductive substrate in situ.

As indicated above, one or more of $R_1$, $R_3$, and $R_5$ in the block copolymer of formula (1) or (2) typically comprises repeat units derived from a vinyl aromatic monomer. For example, the vinyl aromatic monomer can comprise styrene, t-butyl styrene, methyl styrene, a carboxylic acid-functionalized styrene (e.g., vinyl benzoic acid), an amine-functionalized styrene (e.g., diethylamino ethylstyrene), or a mixture thereof. Typically, the vinyl aromatic monomer is styrene.

In some embodiments, each of $R_1$, $R_3$, and $R_5$ comprises repeat units derived from a vinyl aromatic monomer.

By way of non-limiting example, the vinyl aromatic monomer can comprise an unsubstituted vinyl aromatic (optionally styrene or 2-vinyl naphthalene), a vinyl substituted aromatic (optionally alpha-methyl styrene), a ring-substituted vinyl aromatic (optionally wherein the ring-substituted vinyl aromatic comprises 3-methylstyrene, 4-methylstyrene, 2,4-dimethylstyrene, 2,5-dimethylstyrene, 3,5-dimethylstyrene, 2,4,6-trimethylstyrene, 4-tert-butylstyrene, or a mixture thereof), a ring-alkoxylated vinyl aromatic (optionally 4-methoxystyrene or 4-ethoxystyrene), a ring-halogenated vinyl aromatic (optionally wherein the ring-halogenated vinyl aromatic comprises 2-chlorostyrene, 3-chlorostyrene, 4-chlorostyrene, 2,6-dichlorostyrene, 4-bromostyrene, 4-fluorostyrene, or a mixture thereof), a ring-ester-substituted vinyl aromatic (optionally 4-acetoxystyrene), a ring-hydroxylated vinyl aromatic (optionally 4-hydroxystyrene), a ring-amino-substituted vinyl aromatic (optionally 4-amino styrene), a ring-silyl-substituted aromatic (optionally p-dimethylethoxy siloxy styrene), a vinyl pyridine (optionally 2-vinyl pyridine or 4-vinyl pyridine), vinyl carbazole, vinyl ferrocene, or a mixture thereof.

One or more of the high $T_g$ polymers can also comprise repeat units derived from the group consisting of a vinyl monomer, an aromatic monomer, a methacrylic acid monomer, an acrylic monomer, a siloxane monomer, a cinnamic acid monomer, or a mixture thereof.

The high $T_g$ polymers can comprise repeat units derived from a vinyl monomer. By way of non-limiting example, the vinyl monomer can comprise a vinyl ester (optionally vinyl benzoate, vinyl 4-tert-butyl benzoate, vinyl cyclohexanoate, vinyl pivalate, vinyl trifluoroacetate, vinyl butyral), a vinyl amine, a vinyl halide (optionally vinyl chloride or vinyl fluoride), an alkyl vinyl ether (optionally tert-butyl vinyl ether or cyclohexyl vinyl ether), vinyl pyrrolidone, or a mixture thereof.

Also, one or more of the high $T_g$ polymers can comprise repeat units derived from an aromatic monomer. By way of non-limiting example, the aromatic monomer can comprise acenaphthalene or indene, or a mixture thereof.

Further, one or more of the high $T_g$ polymers can comprise repeat units derived from a methacrylic acid monomer. By way of non-limiting example, the methacrylic acid monomer can comprise methacrylic acid anhydride, a methacrylic acid ester, isobornyl methacrylate, trimethylsilyl methacrylate, methacrylonitrile, or a mixture thereof.

For example, one or more of the high $T_g$ polymers can comprise repeat units derived from a methacrylic acid ester monomer. By way of non-limiting example, the methacrylic acid ester monomer can comprise an alkyl methacrylate (optionally methyl methacrylate, ethyl methacrylate, isopropyl methacrylate, isobutyl methacrylate, t-butyl methacrylate, or cyclohexyl methacrylate), an aromatic methacrylate (optionally phenyl methacrylate) an aromatic alkyl methacrylate (optionally benzyl methacrylate), an hydroxyalkyl methacrylate (optionally 2-hydroxyethyl methacrylate or 2-hydroxypropyl methacrylate), or a mixture thereof.

Also, one or more of the high $T_g$ polymers can comprise repeat units derived from an acrylic monomer. By way of non-limiting example, the acrylic monomer can comprise an acrylic acid ester (optionally tert-butyl acrylate, hexyl acrylate, or isobornyl acrylate), acrylonitrile, or a mixture thereof.

For example, one or more of the high $T_g$ polymers can comprise repeat units derived from a siloxane monomer. By way of non-limiting example, the siloxane monomer can comprise diphenylsiloxane.

Further, one or more of the high $T_g$ polymers can comprise repeat units derived from a cinnamic acid monomer. By way of non-limiting example, the cinnamic acid monomer can comprise methyl cinnamate, ethyl cinnamate, cinnamic acid, or a functionalized derivative of cinnamic acid.

Typically, the high $T_g$ polymers can be independently selected from homopolymers, copolymers, block copolymers, and random copolymers. For example, one or more of the high $T_g$ polymers can be a homopolymer. As an additional example, one or more of the high $T_g$ polymers can be a random copolymer or a block copolymer.

Typically, one or more of the low $T_g$ polymers can comprise repeat units selected from the group consisting of an alkene monomer, an acrylic acid monomer, a methacrylic acid monomer, a vinyl ether monomer, a cyclic ether monomer, an ester monomer, a siloxane monomer, or a mixture thereof.

For example, one or more of the low $T_g$ polymers can comprise repeat units derived from an alkene monomer. By way of non-limiting example, the alkene monomer can comprise an alpha-olefin (optionally wherein the alpha-olefin comprises ethylene, propylene, isobutylene, 1-butene, 4-methyl pentene, 1-octene, or a mixture thereof), a diene (optionally wherein the diene comprises 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, 3-butyl-1,3-octadiene), or a halogenated alkene (optionally wherein the halogenated alkene comprises vinylidene chloride, vinylidene fluoride, hexafluoropropylene, cis-chlorobutadiene, or trans-chlorobutadiene), or a mixture thereof.

For example, one or more of the low $T_g$ polymers can comprise repeat units derived from an acrylic acid monomer. By way of non-limiting example, the acrylic acid monomer can comprise an alkyl acrylate (optionally wherein the alkyl acrylate comprises methyl acrylate, ethyl acrylate, propyl acrylate, isopropyl acrylate, butyl acrylate, sec-butyl acrylate, isobutyl acrylate, cyclohexyl acrylate, 2-ethylhexyl acrylate, dodecyl acrylate, hexadecyl acrylate, or a mixture thereof), an arylalkyl acrylate (optionally benzyl acrylate), an alkoxyalkyl acrylate (optionally 2-ethoxyethyl acrylate or 2-methoxyethyl acrylate), a haloalkyl acrylate (optionally 2,2,2-trifluoroethyl acrylate), a cyanoalkyl acrylate (optionally 2-cyanoethyl acrylate), or a mixture thereof.

For example, one or more of the low $T_g$ polymers can comprise repeat units derived from a methacrylic acid monomer. By way of non-limiting example, the methacrylic acid monomer can comprise an alkyl methacrylate (optionally wherein the alkyl methacrylate comprises butyl methacrylate, hexyl methacrylate, 2-ethylhexyl methacrylate, octyl methacrylate, dodecyl methacrylate, hexadecyl methacrylate, octadecyl methacrylate, or a mixture thereof), an aminoalkyl methacrylate (optionally diethylaminoethyl methacrylate or 2-tert-butyl-aminoethyl methacrylate), or a mixture thereof.

For example, one or more of the low $T_g$ polymers can comprise repeat units derived from a vinyl ether acid monomer. By way of non-limiting example, the vinyl ether acid monomer can comprise an alkyl vinyl ether (optionally wherein the alkyl vinyl ether monomer comprises methyl vinyl ether, ethyl vinyl ether, propyl vinyl ether, butyl vinyl ether, isobutyl vinyl ether, 2-ethylhexyl vinyl ether, dodecyl vinyl ether, or a mixture thereof).

For example, one or more of the low $T_g$ polymers can comprise repeat units derived from a cyclic ether monomer. By way of non-limiting example, the cyclic ether monomer can comprise tetrahydrofuran, trimethylene oxide, ethylene oxide, propylene oxide, methyl glycidyl ether, butyl glycidyl ether, allyl glycidyl ether, epibromohydrin, epichlorohydrin, 1,2-epoxybutane, 1,2-epoxyoctane, 1,2-epoxydecane, or a mixture thereof.

For example, one or more of the low $T_g$ polymers can comprise repeat units derived from an ester monomer. By way of non-limiting example, the ester monomer can comprise ethylene malonate, vinyl acetate, vinyl propionate, or a mixture thereof.

For example, one or more of the low $T_g$ polymers can comprise repeat units derived from a siloxane monomer. By way of non-limiting example, the siloxane monomer can comprise dimethylsiloxane, diethylsiloxane, methylethylsiloxane, methylphenylsiloxane, or a mixture thereof.

More typically, one or more of the low $T_g$ polymers comprises repeat units derived from ethylene, propylene, isopropylene, butylene, isobutylene, t-butylene, butadiene, isoprene, neoprene (polychloroprene), or a mixture thereof.

One or more of the low $T_g$ polymers can comprise a fluoroelastomer. By way of non-limiting example, the fluoroelastomer can comprise repeat units derived from tetrafluoroethylene, hexafluoropropylene, vinylidene fluoride, and a mixture thereof.

Typically, the low $T_g$ polymers can be independently selected from a homopolymer, a copolymer, a block copolymer, a random copolymer, or a combination thereof. For example, one or more of the low $T_g$ polymers can be a homopolymer. As an additional example, one or more of the low $T_g$ polymers can be a random copolymer or a block copolymer.

With respect to the block copolymer having the structure of formula (1), (2), (3), or (4), this block copolymer can be a triblock copolymer having the structure of formula (1) wherein each of the polymers of $R_1$ and $R_3$ has a $T_g$ greater than 70° C., and an average number of repeat units of 15 to about 300.

In the block copolymer having the structure of formula (1), (2), (3), or (4), each of the polymers of $R_1$, $R_3$ and $R_5$ can comprise polystyrene, polystyrene sulfonate, poly(t-butyl styrene), poly(styrene-r-styrene sulfonate), or a mixture thereof.

Further, when the block copolymer has a structure of formula (1), the polymer of $R_2$ typically has a $T_g$ less than 0° C. and an average number of repeat units of from about 200 to about 5000.

When the block copolymer has the structure of formula (1), blocks $R_1$ through $R_3$ can be selected in accordance with any of the embodiments set forth above.

Alternatively, the block copolymer having the structure of formula (1), (2), (3), or (4) can be a block copolymer having the structure of formula (2) wherein each of the polymers of $R_1$, $R_3$ and $R_5$ has a $T_g$ greater than 70° C., and an average number of repeat units of from about 15 to about 300.

When the block copolymer has the structure of formula (2), each of the polymers of $R_2$ and $R_4$ can have a $T_g$ less than 0° C. and an average number of repeat units of from about 200 to about 5000.

In the block copolymer having the structure of formula (1), (2), (3), or (4), each of the polymers of $R_2$, $R_4$, and $R_6$ can comprise poly(ethylene), poly(butylene), poly(isobutylene), poly(butadiene), partially sulfonated poly(butadiene), poly(propylene), poly(ethylene-r-propylene), poly(ethylene-r-butylene), poly(ethylene-r-isobutylene), polyisoprene, or a mixture thereof.

When the block copolymer has the structure of formula (2), blocks $R_1$ through $R_5$ can be selected in accordance with any of the embodiments set forth above.

For example, when the block copolymer has the structure of formula (1), each of the polymers of $R_1$ and $R_3$ can comprise polystyrene sulfonate and the polymer of $R_2$ can comprise polyethylene, poly(isobutylene), poly(butylene), or mixtures thereof.

As another example, when the block copolymer has the structure of formula (1), each of the polymers of $R_1$ and $R_3$ comprises polystyrene and the polymer of $R_2$ comprises partially sulfonated poly(butadiene).

In the block copolymer having the structure of formula (1), (2), (3), or (4), each of the polymers of $R_1$ and $R_3$ can comprise poly(t-butyl styrene), each of the polymers of $R_2$, $R_4$, and $R_6$ can comprise poly(ethylene-r-propylene), and the polymer of $R_5$ can comprise poly(styrene-r-styrene sulfonate).

In the block copolymer having the structure of formula (1), (2), (3), or (4), at least one of the polymers of $R_1$, $R_2$, $R_3$, $R_4$, $R_5$ and $R_6$ typically comprises repeat units derived from an anionic monomer. For example, each of the polymers of $R_1$, $R_3$ and $R_5$ can comprise repeat units derived from an anionic monomer. Also, each of the polymers of $R_2$, $R_4$, and $R_6$ can comprise repeat units derived from an anionic monomer.

When the block copolymer has the structure of formula (3) or (4), blocks $R_1$ through $R_6$ can be selected in accordance with any of the embodiments set forth above.

The block copolymer of formula (1), (2), (3), or (4) typically carries an average negative charge per repeat unit of from about −0.01 to about −0.5. For example, the block copolymer may carry an average negative charge per repeat unit of from about −0.1 to about −0.5. More typically, the block copolymer carries an average negative charge per repeat unit of from about −0.1 to about −0.3.

Each of the high $T_g$ polymers $R_1$, $R_3$ and $R_5$ typically has a Young's modulus from about 0.01 GPa to about 50 GPa. More typically, each of the polymers of $R_1$, $R_3$ and $R_5$ has a Young's modulus from about 0.5 GPa to about 5 GPa.

Each of the low $T_g$ polymers of $R_2$, $R_4$, and $R_6$ can typically has a Young's modulus from about 0.001 GPa to about 2 GPa. More typically, each of the polymers of $R_2$, $R_4$, and $R_6$ has a Young's modulus from about 0.01 GPa to about 0.8 GPa.

The polyanionic counterion component can comprise a styrenic block copolymer comprising (a) two or more styrenic blocks independently selected from the group consisting of polystyrene, poly(t-butyl styrene), polymethyl styrene, poly amino styrene, poly carboxylic acid styrene, and mixtures and copolymers thereof, and (b) one or more elastomeric blocks independently selected from the group consisting of polyethylene, polybutylene, polybutadiene, polyisoprene, polyisobutylene, and mixtures and copolymers thereof, and wherein from about 10 to 100 mole percent of the repeat units of the two or more styrenic blocks are functionalized with a negatively charged functional group. The negatively charged functional group can be selected as described in detail above.

Typically, from about 50% to about 70% of the repeat units of the two or more styrenic blocks are sulfonated. More typically, from about 55% to about 65% of the repeat units of the two or more styrenic blocks are sulfonated.

For example, the polyanionic counterion component can comprise a polyanionic triblock copolymer, and more typically a sulfonated triblock copolymer. Non-limiting examples of sulfonated triblock copolymers include sulfonated polystyrene-block-poly(ethylene-r-butylene)-block-polystyrene (SPSEBS), polystyrene-block-polyisobutylene-block-polystyrene (SPSIBS), a block copolymer derived from polystyrene sulfonate and maleic anhydride (PSS-CoMA), and a combination thereof.

For example, the polyanionic counterion component can comprise sulfonated polystyrene-block-poly(ethylene-r-butylene)-block-polystyrene (SPSEBS).

The polyanionic counterion component can comprise polystyrene-block-polyisobutylene-block-polystyrene (SPSIBS).

The polyanionic counterion component can comprise a block copolymer derived from polystyrene sulfonate and maleic anhydride (PSS-CoMA).

Generally, the polyanionic counterion component can comprise a mixture of two or more block copolymers. For example, the polyanionic counterion component can comprise a mixture of two or more block copolymers, each of which is independently selected from formulas (1) or (2) as described above.

More typically, the polyanionic counterion component can comprise a mixture of two or more block copolymers. For example, the polyanionic counterion component can comprise a mixture of two or more block copolymers selected from the group consisting of SPSEBS, SPSIBS, and PSS-CoMA.

The mechanical properties of the polymeric coating are affected by identity and properties of the low $T_g$ (elastomeric) blocks in the block copolymer. Without being bound to a particular theory, it is believed that the rubbery, elastomeric portions of the polyanionic counterion component as described herein provide stress relief when the polymer matrix experiences actuation/volume changes during electrical stimulation, and/or when the coating is exposed to mechanically disruptive forces (e.g., abrasion, disadhesion), thus allowing the polymer matrix/film to temporarily deform as necessary to resist cracking and delamination, while preventing deformation to the extent that the coating undergoes plastic deformation and is unable to return to its original physical state. This feature of the polymeric coatings described herein is surprising, since it is known that similar coatings comprised of electrochemically deposited PEDOT with polystyrene sulfonate (PSS) as the counterion are mechanically stiff, brittle, and prone to cracking and delamination when stressed. This weakness of PEDOT-PSS coatings is overcome by the coatings of the invention that require a mixture of high $T_g$ (stiff) and low $T_g$ (elastomeric) repeat units and/or blocks.

Due to their very different mechanical and chemical properties, the high $T_g$ and low $T_g$ polymers described herein would likely exhibit a high degree of incompatibility in their independent, monomeric or polymeric forms. By joining these blocks and/or repeat units into the same molecule, however, the chemical and physical connectivity between the high $T_g$ and low $T_g$ blocks prevents macroscopic phase separation. Nevertheless, block copolymers comprising two or more blocks with dissimilar properties (e.g., SPSEBS) frequently form a multi-phase separated system, and self-organize into complex structures including but not limited to lamellar, cylindrical, hexagonal-packed cylinder, and body-centered cubic sphere phases. In copolymers where the elastomer is the primary constituent, polystyrene forms separated micro/nano-domains dispersed in the elastomer phase. These materials are members of the family of thermoplastic elastomers, and their excellent thermomechanical properties are associated with multiphase morphology of polystyrene micro-domains dispersed in a rubbery matrix. They exhibit many of the physical properties of rubbers, such as softness, flexibility and resilience, that are balanced by the presence of the relatively harder and stiffer styrenic segments, which can be aligned, oriented, and/or covalently crosslinked between macromolecular chains to further modulate the mechanical properties as desired for a particular target application.

The polyanionic counterion component can also comprise a random copolymer, wherein the random copolymer comprises: (a) styrenic repeat units selected from the group consisting of styrene, t-butyl styrene, methyl styrene, a carboxylic acid-functionalized styrene (e.g., vinyl benzoic acid), an amine-functionalized styrene (e.g., diethylamino ethylstyrene), and mixtures and copolymers thereof, and (b) elastomeric repeat units selected from the group consisting of polyethylene, polybutylene, polybutadiene, polyisopropene, polyisobutylene, and mixtures thereof, and wherein from about 10 to 100 mole percent of the repeat units are functionalized with a negatively charged functional group, which can be selected as described in detail above, and wherein the mole percentage is calculated on the basis of the number of styrenic repeat units.

Typically, from about 50 to about 70 mole percent of the repeat units of the random copolymer are sulfonated, wherein the mole percentage is calculated on the basis of the number of styrenic repeat units. More typically, from about 55% to about 65% of the repeat units are sulfonated, wherein the mole percentage is calculated on the basis of the number of styrenic repeat units.

Particularly, the polyanionic counterion component can comprise sulfonated polystyrene-r-ethylene (SPSE).

The polymerization mixture can further comprise a secondary counterion component.

The secondary counterion component can comprise a negatively charged functional group which can be selected as described in detail above.

By way of non-limiting example, the secondary counterion component can comprise polyvinyl sulfonate, polystyrene sulfonate, polyallyl sulfonate, polyethyl acrylate sulfonate, polybutyl acrylate sulfonate, polyacryl sulfonate, polymethacryl sulfonate, poly-2-acrylamide-2-methylpropane sulfonate, polyisoprene sulfonate, polyvinyl carboxylate, polystyrene carboxylate, polyallyl carboxylate, polyacryl carboxylate, polymethacryl carboxylate, poly-2-acrylamide-2-methylpropane carboxylate, polyisoprene carboxylate, polyacrylates, polyamino acids (e.g., polyglutamates), polydopamine, sulfonated poly ether ether ketone (S-PEEK), sulfonated polyurethanes (polyurethane ionomers), or a mixture thereof.

More typically, the secondary counterion component comprises sulfonic acid, fluorosulfonate, toluene sulfonate, taurine, anthraquinone sulfonate, vinyl sulfonate, 2-acrylamido-2-methyl-1-propanesulfonic acid, polystyrene sulfonate, polyvinyl sulfonate, sulfonated polytetrafluoroethylene, polyanetholesulfonic acid, a salt or functionalized derivative thereof, or a mixture thereof.

The secondary counterion component can comprise polystyrene sulfonate, either alone or in combination with one or more additional species.

Also, the secondary counterion component can comprise paratoluene sulfonate (pTS), 4-vinylbenzenesulfonate, vinyl sulfonate, a polymer thereof, or a combination thereof. The secondary counterion component can comprise sulfonated polytetrafluoroethylene (sold under the trade name NAFION).

The secondary counterion component can comprise a block copolymer derived from polystyrene sulfonate and maleic anhydride (PSS-CoMA). Further, the secondary counterion component can comprise a mixture of polystyrene sulfonate and PSS-CoMA.

As an example, the polyanionic counterion component comprises a copolymer selected from the group consisting of SPSEBS, SPSIBS, and SPSE, and the secondary counterion component comprises polystyrene sulfonate, PSS-CoMA, or a mixture thereof.

For example, the polyanionic counterion component comprises SPSEBS and the secondary counterion component comprises polystyrene sulfonate.

Further, the polyanionic counterion component can comprise SPSIBS and the secondary counterion component can comprise polystyrene sulfonate.

The polyanionic counterion component can comprise SPSE and the secondary counterion component comprises polystyrene sulfonate.

As another example, the polyanionic counterion component comprises SPSEBS and the secondary counterion component comprises PSS-CoMA.

As a further example, the polyanionic counterion component comprises SPSIBS and the secondary counterion component PSS-CoMA.

The polyanionic counterion component can comprise SPSE and the secondary counterion component can comprise PSS-CoMA.

The secondary counterion component can comprise a polyanionic copolymer, a polyanionic block copolymer, a polyanionic multi-block copolymer, or a combination thereof wherein one or more of the repeat units or blocks are functionalized with a negatively charged functional group. The negatively charged functional group can be selected as described in detail above.

For example, the secondary counterion component can comprise a copolymer or block-copolymer selected from the group consisting of sulfonated polystyrene-ethylene, sulfonated polystyrene-butadiene, sulfonated polystyrene-isoprene, and a combination thereof.

The secondary counterion component can comprise a random copolymer comprising a negatively charged functional group. The negatively charged functional group can be selected as described in detail above.

Usually, the random copolymer comprises (a) styrenic repeat units selected from the group consisting of styrene, t-butyl styrene, methyl styrene, a carboxylic acid-functionalized styrene (e.g., vinyl benzoic acid), an amine-functionalized styrene (e.g., diethylamino ethylstyrene), and mixtures thereof, and (b) elastomeric repeat units selected from the group consisting of polyethylene, polybutylene, polybutadiene, polyisopropene, polyisobutylene, and mixtures thereof, wherein from about 10 to 100 mole percent of the repeat units are functionalized with a negatively charged functional group. The negatively charged functional group can be selected as described in detail above.

For example, the secondary counterion component can comprise sulfonated polystyrene-r-ethylene (SPSE).

Generally, the secondary counterion component can comprise a mixture of two or more species of polystyrene sulfonate having different molecular weights.

The secondary counterion component can comprise polystyrene sulfonate (PSS), sulfonated polystyrene-block-poly(ethylene-r-butylene)-block-polystyrene (SPSEBS), polystyrene-block-polyisobutylene-block-polystyrene (SPSIBS), sulfonated polystyrene-r-ethylene (SPSE), a block copolymer derived from polystyrene sulfonate and maleic anhydride (PSS-CoMA), sulfonated polytetrafluoroethylene (sold under the trade name NAFION), polyanetholesulfonic acid, sulfonated poly ether ether ketone (S-PEEK), sulfonated polyurethanes (polyurethane ionomers), poly(2-acrylamido-2-methyl-1-propanesulfonic acid), polyvinyl sulfonate, sulfonated polytetrafluoroethylene, a salt or functionalized derivative thereof, or a mixture thereof.

The secondary counterion component can comprise carbon nanotubes functionalized with a negatively charged functional group. which can be selected as described in detail above.

The secondary counterion component can comprise carbon nanotubes functionalized with polyaminobenzene sulfonate.

The secondary counterion component can comprise functionalized carbon nanotubes in combination with one or more additional polyanionic species as described above. Typically, the one or more additional polyanionic species are selected from the group consisting of polystyrene sulfonate (PSS), sulfonated polystyrene-block-poly(ethylene-r-butylene)-block-polystyrene (SPSEBS), polystyrene-block-polyisobutylene-block-polystyrene (SPSIBS), sulfonated polystyrene-r-ethylene (SPSE), a block copolymer derived from polystyrene sulfonate and maleic anhydride (PSS-CoMA), sulfonated polytetrafluoroethylene, salts and functionalized derivatives thereof, and mixtures thereof.

As set forth above, one aspect of the present invention is directed to a coated electrode comprising an electrically conductive substrate and a polymeric coating, wherein the polymeric coating comprises a reaction product of a polymerization mixture comprising (a) a conductive monomer or a conductive polymer, and (b) a polyanionic counterion component.

Generally, conductive polymers comprise multiple conducting repeat units assembled into chains with conjugated alternating single and double carbon-carbon bonds. Conductive polymers are also sometimes referred to as inherently or intrinsically conducting polymers, electroactive polymers, or conjugated polymers. Conductive polymers are ideally suited for joining or interfacing electronic and ionic systems, because they are capable of conducting both electronic and ionic charge. Conductive polymers can also utilize highly effective and efficient charge storage and transfer mechanisms, similar to capacitors. Without being bound to a particular theory, it is believed that conductive polymers facilitate efficient charge transport through delocalized electrons across conjugated alternating double-single carbon-carbon bonds along the molecular backbone.

Typically, the conductive monomer or the conductive polymer is cationic. For example, when the polymerization mixture comprises a conductive polymer, the conductive polymer typically carries an average charge per repeat unit of from about +0.1 to about +1.0. More typically, the conductive polymer carries an average charge per repeat unit of from about +0.25 to about +0.5, and most typically an average charge per repeat unit of about +0.33.

The conductive polymer can comprise a polyacetylene, a poly(vinyl alcohol), a poly(fluorene), a polyphenylene, a polyphenylene vinylene, a polypyrene, a polyazulene, a polynaphthalene, a poly(pyrrole), a polycarbazole, a polyindole, a polyazepine, a polyaniline, a polyacene, a polythiophene, a polythiophene vinylene, a poly(p-phenylene sulfide), a polypyridine, or functionalized derivatives, precursors or blends thereof.

Usually, the conductive polymer comprises poly(3,4-ethylenedioxythiophene), or a functionalized derivative thereof. For example, the conductive polymer can be derived from 3,4-ethylenedioxythiophene.

Alternatively, the conductive polymer can be derived from a functionalized derivative of 3,4-ethylenedioxythiophene (EDOT) selected from the group consisting of hydroxymethyl-EDOT, EDOT-vinyl, EDOT-ether allyl, EDOT-COOH, EDOT-MeOH, EDOT-silane, EDOT-vinyl, EDOT-acrylate, EDOT-sulfonate, EDOT-amine, and EDOT-amide. More typically, the functionalized derivative of 3,4-ethylenedioxythiophene (EDOT) is selected from the group consisting of hydroxymethyl-EDOT, EDOT-vinyl, EDOT-ether allyl, and EDOT-acrylate.

The conductive polymer can comprise poly(hexylthiophene), or a salt or functionalized derivative thereof. The conductive polymer can comprise poly-4-vinylpyridine. The conductive polymer can comprise poly(diallyldimethylammonium chloride).

Typically, the conductive polymer is formed by electropolymerization.

The conductive monomer can comprise acetylene, fluorene, para-phenylene, pyrene, pyrrole, carbazole, indole, phenyl azide, aniline, thiophene, pyridine, or a mixture or functionalized derivative thereof.

The conductive monomer can comprise 3,4-ethylenedioxythiophene or a functionalized derivative thereof. For example, the conductive monomer can comprise 3,4-ethylenedioxythiophene, hydroxymethyl-EDOT, EDOT-vinyl, EDOT-ether allyl, EDOT-COOH, EDOT-MeOH, EDOT-silane, EDOT-vinyl, EDOT-acrylate, EDOT-silane, EDOT-sulfonate, EDOT-amine, EDOT-amide, ProDOT (3,4-Propylenedioxythiophene), 3,4-(2,2-Dimethylpropylenedioxy)thiophene, 3,4-(2',2'-Diethylpropylene)dioxythiophene, or dimerized or trimerized derivatives of EDOT, such as bi-EDOT or tri-EDOT. More typically, the functionalized derivative of 3,4-ethylenedioxythiophene (EDOT) is selected from the group consisting of hydroxymethyl-EDOT, EDOT-vinyl, EDOT-ether allyl, and EDOT-acrylate.

Alternatively, the conductive monomer can comprise functionalized derivative of 3,4-ethylenedioxythiophene (EDOT) selected from the group consisting of hydroxymethyl-EDOT, EDOT-vinyl, EDOT-ether allyl, and EDOT-acrylate. More typically, the conductive monomer can comprise a functionalized derivative of 3,4-ethylenedioxythiophene EDOT comprising an alkene functional group.

The conductive monomer can comprise a mixture of EDOT and a functionalized EDOT derivative. Typically, the molar ratio of EDOT to the functionalized EDOT derivative is from about 0.5:1 to about 10:1. More typically, the molar ratio of EDOT to the functionalized EDOT derivative is from about 0.5:1 to about 2:1.

The conductive monomer can comprise hexylthiophene or a functionalized derivative thereof. The conductive polymer can comprise 4-vinylpyridine. Further, the conductive polymer can comprise 3-methyl thiophene.

The polymerization mixture can further comprise a crosslinking component.

The crosslinking component typically comprises a monomer functionalized with a group selected from silane, acrylate, a derivative thereof, and a combination thereof.

For example, the crosslinking component can comprise a silane-functionalized monomer. Typically, the crosslinking monomer comprises a vinyl silane, an alkoxy silane, an ethoxy silane, an isocyanatosilane, or another functionalized crosslinkable silane, such as a hydroxy-functional, mercapto-functional or amino-functional silane. More typically, the crosslinking monomer is selected from the group consisting of vinyl trimethoxysilane (VTMS), (3-Aminopropyl) triethoxysilane (APTES), and a combination thereof.

The crosslinking component can comprise an acrylate-functionalized monomer. For example, the crosslinking component can comprise an acrylate-functionalized monomer selected from the group consisting of ethylene glycol di-acrylate (EGDA), poly(ethylene glycol di-acrylate) (PEDGA), ethylene glycol dimethacrylate (EGDMA), poly(ethylene glycol dimethacrylate) (PEGDMA), and a combination thereof.

The polymerization mixture can further comprise a surfactant.

When mixing the various components of the polymerization mixture, it is sometimes advantageous to include a solubilizing agent, such as a surfactant. In general, and although there are some exceptions to this rule, the conductive polymers and conductive monomers described herein tend to be hydrophobic, while the polyanionic counterions and secondary counterions described herein tend to be hydrophilic. Surfactants can be employed to create an emulsion or colloidal suspension where, even with very different levels of hydrophobicity/hydrophilicity, multiple reagents can be effectively held in a partially solvated state through interaction with the amphiphilic surfactant molecules.

The surfactant component can comprise one or more nonionic, cationic, anionic, zwitterionic, amphoteric surfactants, or a combination thereof. Typically, the surfactant component comprises a nonionic surfactant.

The nonionic surfactant is typically selected from the group consisting of polaxamers, polyoxyethylene oleyl ethers, polysorbitan, and polyoxyethylene derivatives of sorbitan monolaurate.

For example, the nonionic surfactant can comprise a poloxypropylene-polyoxyethylene polaxamer (sold under the trade name PLURONIC F-68).

The nonionic surfactant can comprise a polyoxyethylene glycol alkyl ether. For example, the nonionic surfactant can comprise polyethylene glycol octadecyl ether (sold under the trade name BRIJ 78).

The nonionic surfactant can comprise a polyoxyethylene derivative of sorbitan monolaurate. For example, the nonionic surfactant can comprise polyoxyethylene (60 or 80) sorbitan monolaurate (sold under the trade names TWEEN 60 and TWEEN 80).

As set forth above, one aspect of the present invention is directed to a coated electrode comprising an electrically conductive substrate and a polymeric coating.

By way of non-limiting example, the electrically conductive substrate can comprise a carbon nitride, a carbon cloth, a carbon paper, a carbon screen printed electrode, a carbon black, a carbon powder, a carbon fiber, a carbon nanotube, a diamond-coated conductor, a glassy carbon, a mesoporous carbon, a graphite, or a combination thereof.

The electrically conductive substrate can comprise a non-metallic inorganic material. For example, the non-metallic inorganic material can comprise a metal oxide, a metal nitride, a ceramic, a metalloid, or a combination thereof. More typically, the non-metallic inorganic material comprises a metalloid selected from the group consisting of silicon, carbon, and a combination thereof.

The electrically conductive substrate can comprise a metal oxide. For example, the metal oxide can comprise aluminum, titanium, zirconium, hafnium, tantalum, molybdenum, tungsten, rhenium, iridium, or a combination thereof.

The electrically conductive substrate can comprise a ceramic. For example, the ceramic can comprise a silicon nitride, a silicon carbide, a silicon oxide, a calcium phosphate, or a combination thereof.

The electrically conductive substrate can comprise a metal selected from the group consisting of a noble metal, a transition metal, or a combination thereof. For example, the metal can be selected from the group consisting of gold, platinum, palladium, iridium, osmium, rhodium, titanium, tantalum, tungsten, ruthenium, magnesium, iron, and a combination thereof.

The electrically conductive substrate can comprise a non-noble metal. For example, the non-noble metal can be selected from the group consisting of titanium, tantalum, and a combination thereof.

The electrically conductive substrate can comprise a metal alloy. Typically, the metal alloy comprises at least one noble metal and at least one transition metal. By way of non-limiting example, the metal alloy can comprise iron, sulfur, manganese, and molybdenum; iron and chromium; nickel and titanium; nickel and cobalt; cobalt and chromium; cobalt, chromium and iron; cobalt, chromium and nickel; cobalt, chromium, nickel and tungsten; nickel and chromium; magnesium and iron; or a combination thereof. For example, the metal alloy can comprise nickel and cobalt. The metal alloy can also be a stainless steel alloy selected from the group consisting of stainless steel 304L, stainless steel 316L, stainless steel 316LVM, stainless steel MP35N, stainless steel 35NLT, and a combination thereof.

Generally, the conductive substrates can have almost any form, including but not limited to metal pieces, coupons, meshes, wires, blocks, tubes, and/or spheres. More typically, the conductive substrate comprises all or part of one or more electrodes on a device, for example a medical device.

Typically, the electrically conductive substrate is coated with a polymeric coating having a thickness of from about 200 nm to about 10 μm. More typically, the electrically conductive substrate is coated with a polymeric coating having a thickness of from about 500 nm to about 5 μm.

Generally, the polymeric coatings described herein comprise a matrix of conducting polymer chains intertwined with polyanionic counterion molecules, forming a nanoporous, very high surface area matrix or network. Typically, the polymeric coating is localized exclusively to the conductive substrate, or to the conductive regions of the substrate. Without being bound to a particular theory, it is believed that the conducting polymer coatings described herein are electronically and ionically conductive due to conjugated alternating double and single bonds with delocalized electrons in pi-pi orbitals along the carbon backbone of the conducting polymer chains, and are charge balanced by the physical and electro-ionic interaction between the conducting polymer molecules and the polyanionic counterion and/or secondary counterion molecules.

It is believed that the high stability and durability of the polymeric coatings described herein are imparted by the combined action of (a) the mechanical and structural properties of the conducting polymer or conducting monomer and polymeric counterions, (b) the electrostatic bonds between the conducting polymer or conducting monomer and counterion polymer chains and the metal surface, (c) dipole alignment between the conducting polymer or conducting monomer and metal surface, (d) in some embodiments, surfactant-mediated phase-separation and phase ordering/templating in the polymerization solution and the resulting deposited coating, respectively, and in some embodiments by the addition of (e) cohesive molecular crosslinks throughout the conducting polymer or conducting monomer/counterion matrix, and by (f) adhesive covalent bonding of the coating to the underlying metal substrate.

Another aspect of the present invention is directed to a method of preparing the coated electrode set forth above.

Generally, the method comprises (1) preparing a polymerization mixture comprising (a) a conductive monomer or a conductive polymer; and (b) a polyanionic counterion component; and (2) electrochemically polymerizing the polymerization mixture to form a polymeric coating on an electrically conductive substrate.

The conductive monomer or conductive polymer, polyanionic counterion component, and electrically conductive substrate can be selected as set forth in detail above. Additionally, as set forth in detail above, the polymerization mixture can comprise one or more additional components, including but not limited to a secondary counterion component, a surfactant component, and a crosslinking component.

Generally, conductive polymers can be polymerized from their constituent monomers by oxidation reactions driven by electrochemical synthesis at an anode in a liquid electrolyte, or alternatively by chemical synthesis in the presence of an oxidant in liquid or gas. Conducting polymers are commonly manifest as thin films or coatings on conductive or non-conductive substrates and as micro/nanoparticles on a substrate/or surface, or as a dispersion or colloidal suspension in an aqueous or organic solvent.

Electrochemically polymerized thin film conducting polymer coatings electrodeposited onto conductive substrates, such as the coatings described herein, exhibit a high relative conductivity for a conducting polymer-based material, due to a high proportion of conducting polymer chains that are aligned and oriented in a manner that optimizes electronic and ionic conduction. This stands in contrast to conducting polymer coatings or materials obtained by chemical oxidative polymerization, in which the polymer chains show less orientation and alignment, and the coating exhibits a lower conductivity than electrochemically polymerized conducting polymer coatings.

In a typical embodiment, the polymeric coating is applied to the conductive substrate by electrodeposition.

Electrochemical deposition of conductive polymers is the preferred deposition technique for applying the disclosed conductive polymer coatings to conductive substrates. Electrodeposited coatings can be localized only and specifically to the conductive regions of a substrate. As a result, electrodeposited coatings are highly conformal, completely covering the conductive area with a coating of uniform thickness and composition, and without the disadvantages of spraying or dipping technologies discussed above. Furthermore, the electrodeposition process can usually be performed under normal air pressure, and in aqueous or similar conditions that do not require the use of dangerous or environmentally hazardous chemicals required by chemical oxidative polymerization.

The polymeric coating can be formed in situ.

For example, the electrochemical polymerization reaction can be carried out by immersing the conductive substrate in the polymerization mixture. When electrical charge is delivered to the conductive substrate, polymerization is initiated and a polymeric coating is electrodeposited in situ onto the conductive portions of the substrate that are immersed in the polymerization mixture.

The various components of the polymerization mixture are typically prepared in the presence of a solvent component. For example, the polymerization mixture can be prepared in an aqueous environment (i.e., in the presence of water). More typically, the polymerization mixture is prepared in the presence of an organic solvent.

The organic solvent can be a polar organic solvent. More typically, the organic solvent is an aprotic organic solvent. By way of non-limiting example, the aprotic organic solvent can be selected from the group consisting of acetonitrile, dichloromethane, dimethylsulfoxide, acetone, dimethylformamide, and a combination thereof.

The solvent component can comprise a polar protic solvent. By way of non-limiting example, the polar protic solvent is typically selected from the group consisting of water, isopropanol, methanol, ethanol, and a combination thereof.

The solvent component can comprise a mixture of water and one or more organic solvents. For example, the solvent component can comprise a mixture of water and one or more aprotic organic solvents. In a typical embodiment, the solvent component comprises a mixture of water and acetonitrile.

Where the solvent component comprises water and an aprotic organic solvent, the volumetric ratio of water to the aprotic organic solvent is typically from about 1:10 to about 10:1. More typically, the volumetric ratio of water to the aprotic organic solvent is from about 1:3 to about 3:1.

The various components of the polymerization mixture can be mixed or combined in any order.

For example, a conducting polymer precursor solution comprising (a) the conductive polymer or conductive monomer and (b) the solvent component is typically prepared separately from the other components of the polymerization mixture. In the conducting polymer precursor solution, the concentration of the conductive polymer or conductive monomer typically ranges from about 0.001M to about 1M, more typically from about 0.01M to about 0.2M, and is more typically about 0.015M.

To improve the stability of the conducting polymer precursor solution, a surfactant is typically added. The conducting polymer precursor solution can be vortexed, agitated, or stirred.

A solution comprising the polyanionic counterion component, typically in a concentration of from about 0.001M to about 1M, more typically from about 0.01M to about 0.1M, can be prepared separately from the conducting polymer precursor solution. The solution comprising the polyanionic counterion component is combined with the conducting polymer precursor solution to form the polymerization mixture.

The polymerization mixture can also undergo one or more preprocessing steps prior to the electrochemical polymerization. For example, the polymerization mixture can be vortexed, agitated, or stirred prior to the electrochemical polymerization step.

The temperature of the polymerization mixture is typically maintained at from about 20° C. to about 40° C. prior to the electrochemical polymerization step.

The pH of the polymerization mixture is typically adjusted to a range of from about 2.5 to about 10 prior to the electrochemical polymerization step.

Prior to deposition of the polymeric coating, the conductive substrate should be as uniform as possible, and should be clean and free of organic material/molecules, dust and other contaminants so that the coating comes into direct and complete contact with the underlying conductive substrate. Substrate cleaning can be achieved a number of ways with varying degrees of harshness, including but not limited to rinsing and/or ultrasonicating in water or soapy water, exposure to organic solvents such as acetone or alcohol, hydrogen peroxide, acids or etching solutions (e.g. Pirhana etch), exposure to reactive plasma cleaning/etching such as $CF_4$, or microgrit blasting with media such as sodium bicarbonate, silica, and alumina. After cleaning, the conductive substrate is typically dried under a stream of nitrogen or argon to limit exposure to oxygen, which can contaminate the cleaned surface. It is sometimes preferable to store the cleaned substrates (prior to coating) in oxygen-free environments (e.g., a glove box purged with nitrogen).

The preparation methods described herein can further include the step of roughening the conductive substrate prior to the electrochemical polymerization step. Roughening the conductive substrate helps to expose the preferred surface and/or to improve coating uniformity, conformality, and adhesion to the substrate. Typically, surfaces with micro/nano scale uniform roughness are preferred.

For example, the conductive substrate is chemically roughened using an etching solution. Alternatively, the conductive substrate can be electrochemically roughened. Typically, the electrochemical roughening step comprises exposing the conductive substrate to voltage or current pulsing or cycling in a solution selected from the group consisting of hydrochloric acid, sulfuric acid, ethanolic saline, and a combination thereof. As a further alternative, the conductive substrate can be mechanically roughened. The mechanical roughening is typically conducted by micro-grit blasting with media including but not limited to silica, alumina, and/or sodium bicarbonate.

The surface of the conductive substrate is modified with an organic molecule layer. Non-limiting examples of an organic molecule layer include an oxide layer, a monolayer, or self-assembled monolayer, or a tie layer. Organic molecule surface modification can be employed to modulate physical properties of the coated substrate including but not limited to coating adhesion, conductivity, and uniformity. Non-limiting examples of surface functional groups include thiols and silanes. Molecular modification of the surface of the conductive substrate can be achieved in a number of ways, including but not limited to reactive plasma exposure, soaking/dip-coating or micro/nano spray with molecular solution, electrochemical mediated oxidation/reduction of a metal surface, and/or electro-grafting of molecular species.

Typically, it is preferable to use a constant current or voltage to drive the electrochemical polymerization reaction. The application of constant current or voltage typically results in a single layer polymer matrix, wherein the thickness of the layer is dependent upon the total amount of charge used to drive the electrochemical polymerization.

A potentio-dynamic electro-deposition method can be used where voltage is swept or cycled from a low to high voltage. The application of cyclic voltage typically results in a coating with multiple interfaced layers of polymer matrix.

The electrochemical polymerization step is typically carried out inside a container or vessel containing at least 2 electrodes. More typically, the container or vessel comprises a working or sense electrode (WE); a counter or return electrode (CE) having approximately 10× the surface area of the WE, and which is preferably made of platinum, platinized titanium, or platinized niobium; and, optionally, a reference electrode (RE), which is preferably a KCl saturated $Ag/AgCl_2$ or calomel reference electrode.

The electrochemical polymerization step is typically carried out at room temperature (from about 20° C. to about 40° C.). In some cases, the polymerization solution is gently agitated or stirred during the electrochemical polymerization step. Additionally, the pH of the polymerization solution is typically maintained within a range of from about 2.5 to about 10 during the electrochemical polymerization step.

In accordance with the methods described above, it has also been discovered that key electrical properties of the coated electrode, such as impedance, can be measured using the same equipment that is employed for coating deposition. As a result, it is possible for deposition of the polymeric coating and quality assurance/acceptance testing of the coated electrode to be conducted simultaneously. This is very desirable, particularly with regard to manufacturing, because it allows for various device components/electrodes can be coated at various stages in the manufacturing process, and is highly cost-efficient and environmentally safe.

As set forth above, the polymerization mixture can optionally comprise a crosslinking component. The crosslinking component typically comprises a monomer functionalized with a group selected from a silane, an acrylate, a derivative thereof, and a combination thereof.

When the crosslinking component comprises a silane functional group, the silane-functionalized monomer (referred to hereinafter as a "silane") is typically incorporated into the conducting polymer coating as a component that is added into the polymerization mixture. When the silane-functionalized monomer is added to the coating precursor solution, it typically is neutral or negatively charged.

Alternatively, following the electrochemical polymerization of the polymerization mixture and deposition of the polymeric coating on to the conductive substrate, the polymeric coating can be dipped, soaked, sprayed or otherwise exposed to a silane solution, such that the silane can diffuse into the coating.

If a neutral or negatively charged silane is to be incorporated into the coating by diffusion, this can typically be accomplished by passive diffusion, wherein the polymeric coating is submerged in the silane solution. Under this method, mass transport is expected to mediate filing and coating of the nano/micro scale pores of the conducting polymer coating with silane. Alternatively, for negatively-charged silanes, electrochemistry-mediated active diffusion can be used, wherein the conductive substrate is electrically connected as the anode within a 2 or 3-electrode voltammetry cell, and voltage or current (positive bias) is applied to the circuit. Under this method, the negatively charged silane will be attracted to the anode (i.e., the conductive substrate), and will therefore be drawn into the polymeric coating matrix.

Once the silane is incorporated or diffused within the conducting polymer coating matrix, the coated substrate can be cured/crosslinked by rinsing in water, followed by air drying. As an alternative to air drying, the coated substrate can be placed in an oven at approximately 40-60° C., which facilitates the condensation, hydrogen bonding, and silane-oxygen covalent bond formation reactions.

The crosslinking component can comprise an acrylate functional group. When an acrylate functional group is used, it is preferable for the crosslinking component to additionally comprise a di-functional molecule with terminal unsaturated alkenes or acrylates. A wide variety of di-functional molecules with terminal unsaturated alkenes or acrylates can be used for acrylate crosslinking, as understood by those skilled in the art. Non-limiting examples of suitable di-functional molecules with terminal unsaturated alkenes or acrylates include ethylene glycol di-acrylate (EGDA), poly ethylene glycol dimethacrylate (PEGDMA), ethylene glycol dimethacrylate (EGDMA), poly ethylene glycol di-acrylate (PEGDA), vinyl terminated poly(dimethylsiloxane), and a combination thereof. Alternatively, the polymerization mixture can comprise a conductive monomer selected from an alkene or acrylate-derivatized EDOT species.

To achieve acrylate crosslinking of conducting polymer coatings, following the electrochemical polymerization step, the coated electrode should be exposed to (e.g., by soaking, dipping, or spraying) a solution containing a free radical initiator molecule. After exposing the coated electrode to a free radical initiator, it is also typical to expose the initiator-infused coated electrode to heat or UV light to activate the crosslinking or curing reaction.

Another aspect of the present invention is directed to a medical device comprising the coated electrode described above. For example, the medical device can be an implantable medical device.

Having described the invention in detail, it will be apparent that modifications and variations are possible without departing from the scope of the invention defined in the appended claims.

EXAMPLES

The following non-limiting examples are provided to further illustrate the present invention.

Example 1: Preparation of a Polymerization Mixture Comprising EDOT, SPSEBS, and PSS A conducting polymer precursor solution (100 mL) was prepared comprising EDOT (0.015M) in water in a glass beaker. The beaker was placed on a magnetic stir plate, and a magnetic stir bar was used to stir the mixture at a speed fast enough to create a vortex in the center of the mixture, but not so fast that the mixture developed bubbles. While the mixture was being stirred, PLURONIC F68 10% solution (125 µL) was slowly added to stabilize the mixture.

After constant stirring at room temperature for approximately 12 hours, the aqueous EDOT mixture was fully transparent, with no visible globules of undissolved EDOT.

An aqueous solution comprising 30% v/v of polystyrene sulfonate (average molecular weight 70,000) was then added to the aqueous mixture (125 µL)

Following addition of the polystyrene sulfonate solution, a solution of sulfonated polystyrene-block-poly(ethylene-r-butylene)-block-polystyrene (SPSEBS) in a mixture of propanol/dichloroethane solvents (5% vol/vol SPSEBS) added slowly to the EDOT/PSS mixture (125 µL).

The resulting polymerization mixture was clear, and the conducting polymer monomer was fully emulsified.

Example 2: Preparation of a Polymerization Mixture Comprising EDOT, SPSIBS, and PSS A conducting polymer precursor solution (100 mL) was prepared comprising EDOT (0.015 M) in a combination of water and acetonitrile (1:1 volumetric ratio) in a glass beaker. The beaker was placed on a magnetic stir plate, and a magnetic stir bar was used to stir the mixture at a speed fast enough to create a vortex in the center of the mixture, but not so fast that the mixture developed bubbles. While the mixture was being stirred, PLURONIC F68 10% solution (125 µL) was slowly added to stabilize the mixture.

After constant stirring at room temperature for approximately 12 hours, the aqueous EDOT mixture was fully transparent, with no visible globules of undissolved EDOT.

An aqueous solution comprising 30% v/v of polystyrene sulfonate (average molecular weight 70,000) was then added to the aqueous mixture (125 µL).

Following addition of the polystyrene sulfonate solution, a solution of polystyrene-block-polyisobutylene-block-polystyrene (SPSIBS) in a mixture of propanol/dichloroethane solvents (5% vol/vol SPSIBS) added slowly to the EDOT/PSS mixture (100 mL).

The resulting polymerization mixture was clear and the conducting polymer monomer was fully emulsified.

Example 3: Preparation of a Polymerization Mixture Comprising EDOT and EDOT-Acrylate A conducting polymer precursor solution was prepared using a combination of EDOT and EDOT-acrylate. A combination of EDOT (0.001 g) and EDOT-acrylate (0.001 g) was added to a solvent solution (125 µL) comprising water and acetonitrile in a 1:2 vol:vol ratio.

The beaker was placed on a magnetic stir plate, and a magnetic stir bar was used to stir the mixture at a speed fast enough to create a vortex in the center of the mixture, but not so fast that the mixture developed bubbles. While the mixture was being stirred, PLURONIC F68 10% solution (125 µL) was slowly added to stabilize the mixture.

After constant stirring at room temperature for approximately 12 hours, the aqueous EDOT/EDOT-acrylate mixture was fully transparent, with no visible globules of undissolved polymer.

An aqueous solution comprising 30% v/v of polyanetholesulfonic acid (average molecular weight 10,000) was then added to the aqueous mixture (125 µL).

Following addition of the polystyrene sulfonate solution, a solution comprising the styrenic block copolymer NEXAR 9200 (0.001 g) was added slowly to the EDOT/polyanetholesulfonic acid mixture (100 mL).

The resulting polymerization mixture was clear and the conducting polymer monomer was fully emulsified.

Example 4: Preparation and Characterization of the Coated Electrode

A polymerization mixture was prepared using the procedure set forth in Example 1.

A platinum electrode was selected as the conductive substrate. The platinum electrode surface was visually inspected for major defects, and was then cleaned and roughened by microgrit blasting (60 sec at distance of ~1.2 inch with 60-80 psi) with sodium bicarbonate using a VANIMAN SANDSTORM microabrasive sand blaster. The electrode substrate was then cleaned by ultrasonication in isopropanol and acetone.

The polymerization mixture was then transferred to a 3-electrode voltammetry cell connected to a BIO-LOGIC VMP3 potentiostat/galvanostat. The voltammetry cell comprised phosphate buffered saline (PBS, pH ~7.0) as the electrolyte, the platinum electrode (conductive substrate) as the working electrode, a platinized niobium mesh (~10× larger surface area than the working electrode) as the counter electrode, and Ag/AgCl (saturated KCl) reference electrode.

The electrodeposition reaction was initiated by driving the process at a constant current of 0.5 mA/cm$^2$ for a duration of 20 minutes onto the working electrode. The electrodeposition step was carried out at room temperature.

Upon removal from the voltammetry cell, the coated electrode appeared black, and the polymeric coating fully covered the portion of the conductive substrate that was submerged in the coating solution.

The BIO-LOGIC VMP3 potentiostat/galvanostat was used to perform the electrical characterization of the coated electrode.

Electrochemical impedance spectroscopy (EIS) was measured at frequencies from 1-100,000 Hz while applying 5 mV root mean square (RMS) sine wave between the working and counter electrode. Results of the impedance spectroscopy testing for the coated electrode described above are depicted in FIG. 1. Similar tests, conducted on an electrode prepared from a polymerization mixture comprising a solvent mixture of water and acetonitrile (50:50 v/v) were also conducted, and are also depicted in FIG. 1.

Figure 2:
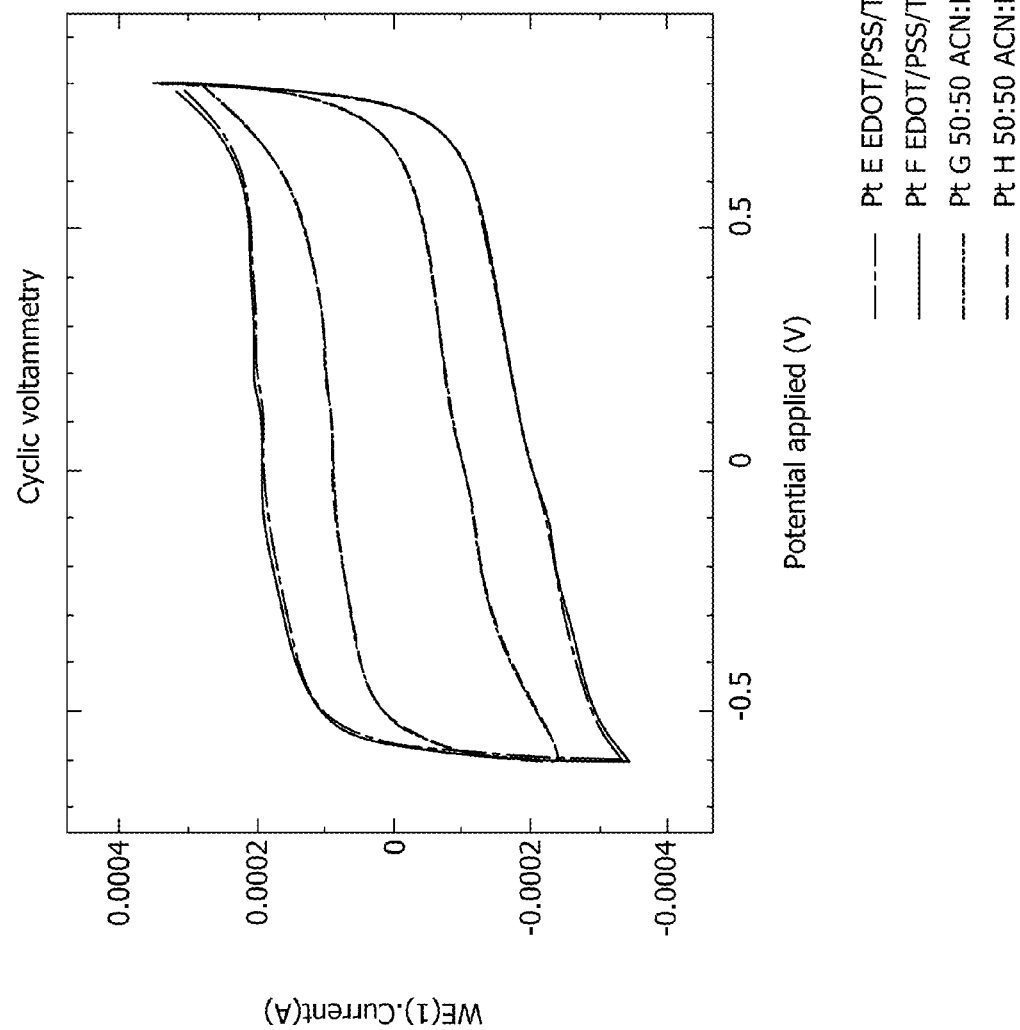
FIG. 2 depicts the results of a cyclic voltammetry test involving the electrodes prepared in Example 4.

Cyclic voltammetry (CV) testing was performed to measure the charge storage and transfer properties of the electrodes. The current was measured as the voltage was cycled from +0.8 to −0.6 V versus the SCE at a rate of 0.1 V/s, starting at 0V. Results of the cyclic voltammetry testing for the coated electrode described above are depicted in FIG. 2. Similar tests, conducted on an electrode prepared from a polymerization mixture comprising a solvent mixture of water and acetonitrile (50:50 v/v) were also conducted, and are also depicted in FIG. 2.

Additionally, it was determined that the coated electrode exhibited greater than a 50% improvement in impedance at frequencies below 1000 Hz and greater than a 100% increase in CSC (the amount of charge that can be stored and delivered over a given voltage and time range, as measured by cyclic voltammetry) as compared to the original, uncoated platinum electrode.

Extended stimulation of electrodes was performed with a NATIONAL INSTRUMENTS data acquisition system (cDAQ-9174) with the appropriate voltage and current cards running LAB VIEW software. A 2-electrode electrochemical cell with phosphate buffered saline (PBS, pH ~7.0) was used as the electrolyte, the platinum conductive substrate as the working electrode, and a platinized niobium mesh as counter electrode. The system sourced 100-400 µs symmetric cathodic-first square waves with voltage magnitude of 1-3V which resulted in a pulse waveform with peak current density of 20 µC/cm$^2$ per phase at a rate of 1000 Hz. The extended stimulation was performed constantly for 100-120 hrs at room temperature. At the stimulation rate, this resulted in delivery of ~100 million pulses per 24 hour period.

The electrical durability of coated substrates were also tested using short-term cyclic voltammetry (CV) or current (I) pulsing-based stress tests. The objective of such short-term stress tests is that by increasing the cycling voltage or current amplitude in sequential rounds of acute electrical stress, the relative durability of the coating types can be discriminated in a short period of time (~1 hour).

Figure 3:
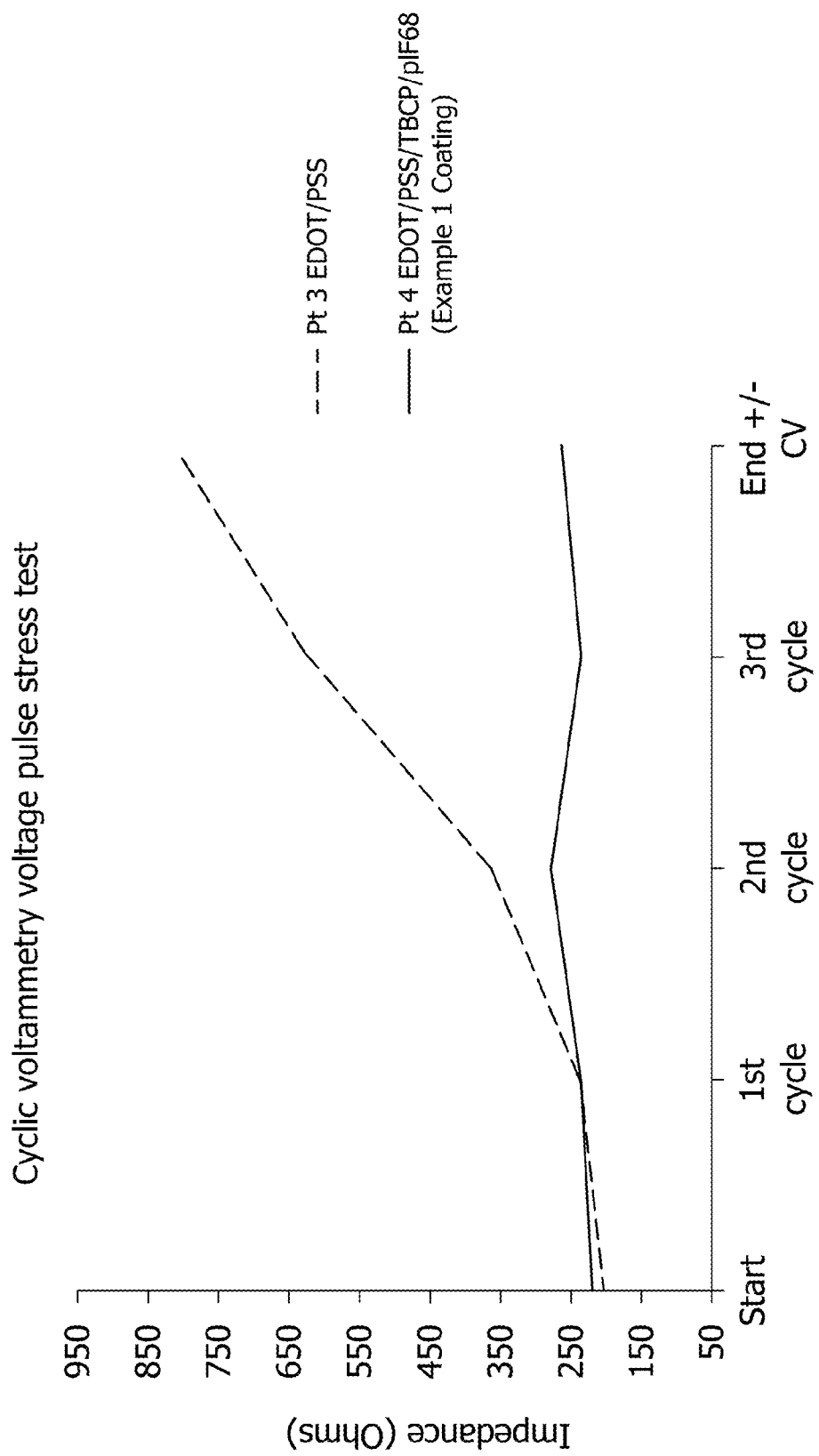
FIGS. 3 and 4 depict the results of a cyclic voltammetry voltage pulse stress test involving the electrodes prepared in Example 4.
Figure 4:
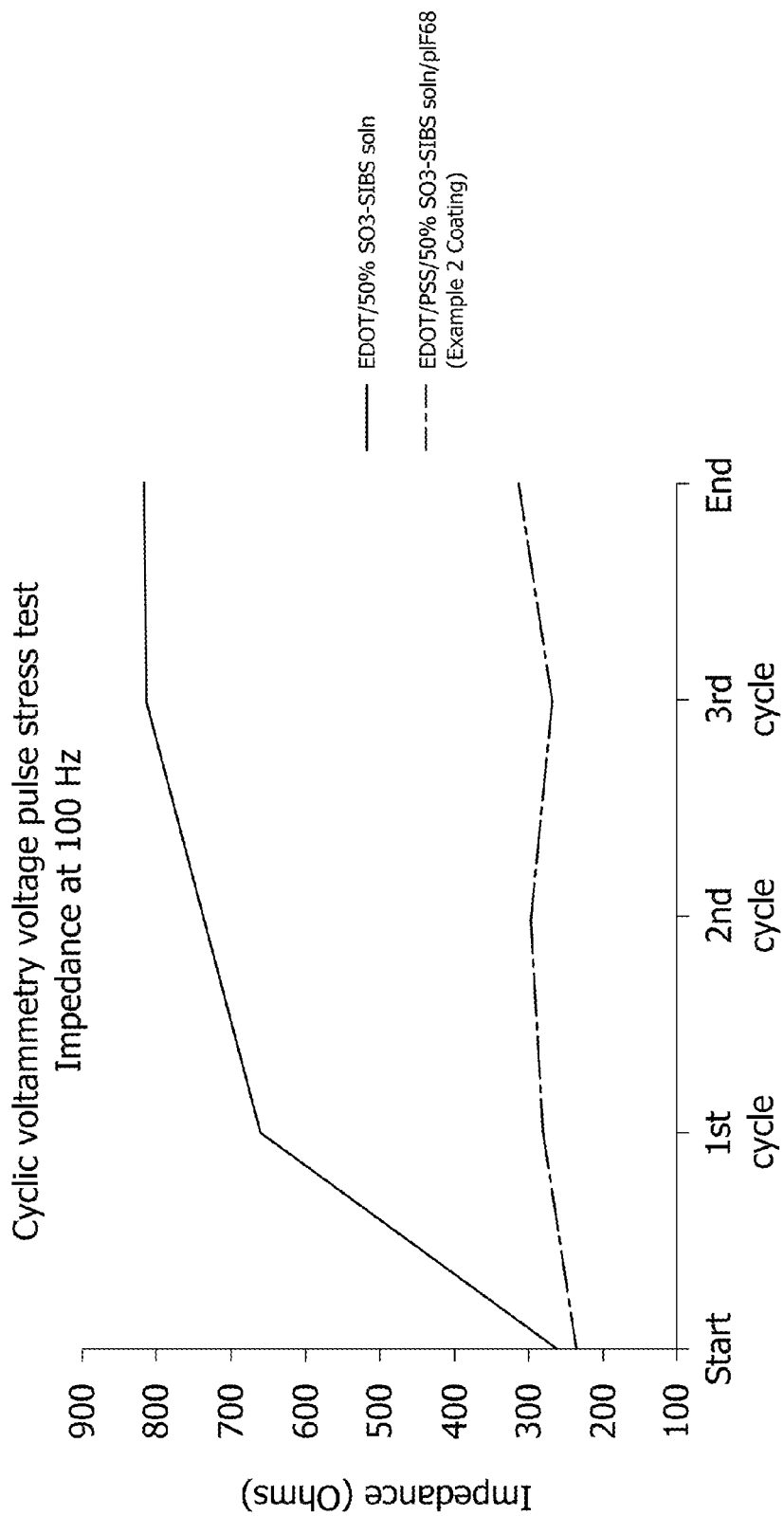

The results of a cyclic voltammetry voltage pulse stress test, in which the coated electrode prepared as described above is compared to a reference electrode comprising a PEDOT/PSS coating, are set forth in FIG. 3. A similar test, conducted on an electrode prepared from the polymerization mixture set forth in Example 2, is set forth in FIG. 4.

Example 5: Preparation of a Polymerization Mixture Comprising a Silane Crosslinking Component A conducting polymer precursor solution was prepared using a combination of EDOT and EDOT-vinyl. A combination of EDOT and EDOT-vinyl (10 mg total, 5:1 molar ratio) was added to a glass beaker comprising a solvent solution (100 mL) of water and acetonitrile in a 1:1 vol:vol ratio.

The beaker was placed on a magnetic stir plate, and a magnetic stir bar was used to stir the mixture at a speed fast enough to create a vortex in the center of the mixture, but not so fast that the mixture developed bubbles. While the mixture was being stirred, PLURONIC F68 10% solution (125 ul) was slowly added to stabilize the mixture.

After constant stirring at room temperature for approximately 18 hours, the aqueous mixture was fully transparent, with no visible globules of undissolved polymer.

Following addition of the polystyrene sulfonate solution, a solution comprising sulfonated polystyrene-block-poly (ethylene-r-butylene)-block-polystyrene (125 µL) was added slowly to the polymerization mixture (100 mL).

A crosslinking component comprising vinyl trimethoxysilane (0.01 g) in water (10 mL) was then added to form the polymerization mixture.

The polymerization mixture was then transferred to a 3-electrode voltammetry cell connected to a potentiostat/galvanostat. The voltammetry cell comprised a platinum working electrode (i.e., the conductive substrate), a platinum return electrode, and a calomel reference electrode. The electrodeposition reaction was initiated by driving the process at a constant current of 0.5 mA/cm$^2$ for a duration of 20 minutes onto the working electrode. The electrodeposition step was carried out at room temperature.

To cure the polymer and initiate the crosslinking reaction, the coated electrode was then dried in an oven at 55° C. for two hours. The polymeric coating exhibited better adhesion to the underlying platinum substrate (as exhibited by both electrical and mechanical stress tests) as compared to the non-crosslinked coated electrode prepared in Example 4.

Example 6: Preparation of a Polymerization Mixture Comprising an Acrylate Crosslinking Component A conducting polymer precursor solution was prepared using a combination of EDOT and EDOT-acrylate (10 mg total, 5:1 molar ratio), which was added to acetonitrile (100 mL) in a glass beaker.

The beaker was placed on a magnetic stir plate, and a magnetic stir bar was used to stir the mixture at a speed fast enough to create a vortex in the center of the mixture, but not so fast that the mixture developed bubbles. While the mixture was being stirred, PLURONIC F68 10% solution (125 µL) was slowly added to stabilize the mixture.

After constant stirring at room temperature for approximately 4 hours, the aqueous mixture was fully transparent, with no visible globules of undissolved polymer.

A crosslinking component comprising ethylene glycol dimethacrylate (0.01 g) in water (10 mL) was then added to form the polymerization mixture.

The polymerization mixture was then transferred to a 3-electrode voltammetry cell connected to a potentiostat/ galvanostat. The voltammetry cell comprised a platinum working electrode (i.e., the conductive substrate), a platinum return electrode, and a calomel reference electrode. The electrodeposition reaction was initiated by driving the process at a constant current of 0.5 mA/cm² for a duration of 20 minutes onto the working electrode. The electrodeposition step was carried out at room temperature.

Following the electrodeposition process, the coated electrode was fully immersed in a hydrogen peroxide solution for 20 minutes. Upon removal from the $H_2O_2$ solution, the coated electrode was placed in an oven to cure at 55° C. for two hours. The polymeric coating exhibited better adhesion to the underlying platinum substrate (as exhibited by both electrical and mechanical stress tests) as compared to the non-crosslinked coated electrode prepared in Example 4.

Example 7: Tape Adhesion Test

The mechanical adhesion of the polymeric coating to the conductive substrate was evaluated using the standard tape adhesion test set forth in ASTM D3359.

Tests were conducted on a coated electrode prepared from the polymerization mixture as set forth in Example 1. For a comparative example, a reference coated electrode was prepared from a polymerization mixture comprising only EDOT and polystyrene sulfonate. Both electrodes were prepared using the electrodeposition procedure set forth in Example 4.

The coated electrodes were exposed to multiple rounds of CV pulse cycles prior to performance of the tape adhesion test. The CV pulse cycling typically causes electromechanical weakening of the polymeric coating, so a coated electrode that can resist this degradation is particularly desirable.

Figure 5:
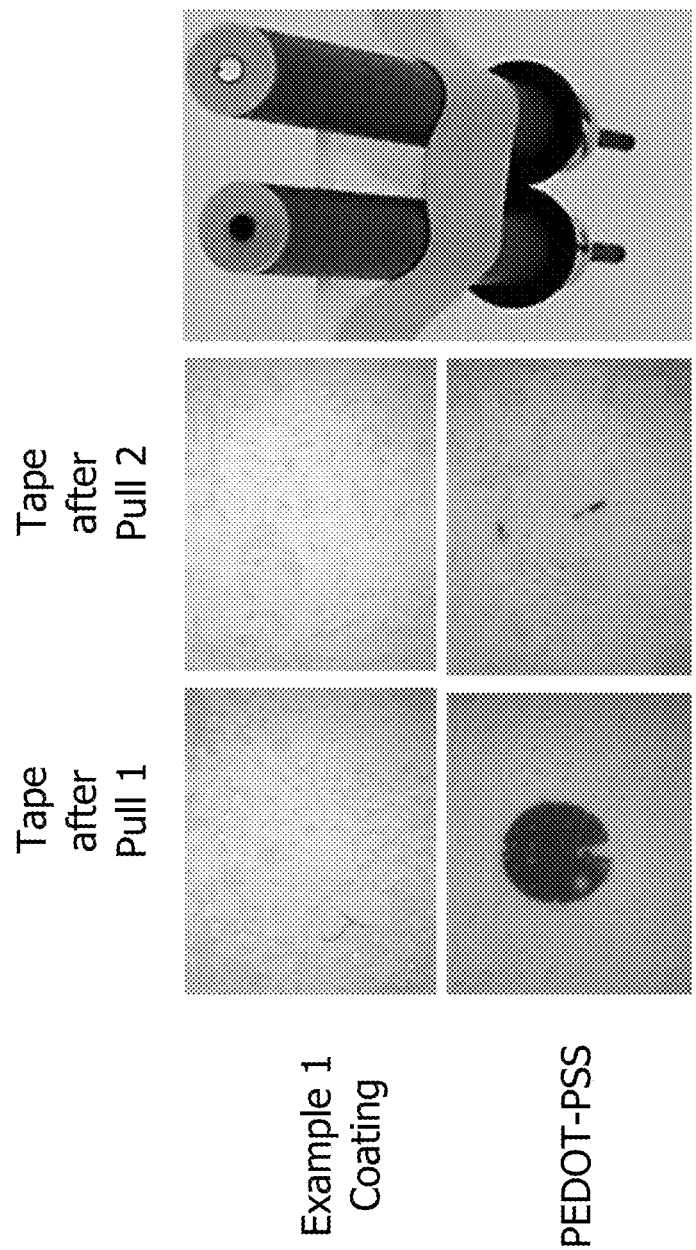
FIG. 5 depicts the results of the ASTM tape adhesion test as described in Example 7.

The results of the tape adhesion test are depicted in FIG. 5. Generally, the coating derived from the Example 1 polymerization mixture did not exhibit any loss of adhesion. The comparative electrode, however, exhibited a significant loss of the PEDOT/PSS coating.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there can be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A coated electrode comprising an electrically conductive substrate and a polymeric coating, wherein the polymeric coating comprises a reaction product of a polymerization mixture comprising:
   a conductive monomer or a conductive polymer; and
   a polyanionic counterion component comprising a block copolymer having the structure of formula (1), (2), (3), or (4):

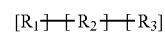
(1)

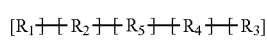
(2)

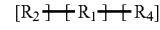
(3)

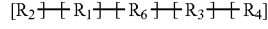
(4)

wherein
   $R_1$, $R_3$, and $R_5$ independently comprise a high glass transition temperature (high $T_g$) polymer having a $T_g$ greater than 50° C. and less than the melting temperature ($T_m$) of the copolymer, and having an average number of repeat units of from about 15 to about 300;
   $R_2$, $R_4$, and $R_6$ independently comprise a low glass transition temperature (low $T_g$) polymer having a $T_g$ less than 30° C., and having an average number of repeat units of from about 200 to about 5000; and
   from about 10 to about 100 mol % of repeat units of the high $T_g$ polymer in $R_1$, $R_3$ and $R_5$ are functionalized with a negatively charged functional group, and/or from about 10 to 100 mol % of repeat units of the low $T_g$ polymer in $R_2$, $R_4$, and $R_6$ are functionalized with a negatively charged functional group.

2. The electrode of claim 1 wherein the block copolymer has the structure of formula (3) or (4).

3. The electrode of claim 1 wherein one or more of $R_1$, $R_3$, and $R_5$ comprises repeat units derived from a vinyl aromatic monomer, the mole percent of the vinyl aromatic monomer in each of $R_1$, $R_3$ and $R_5$ being from about 10 to about 100 mol %.

4. The electrode of claim 3 wherein the vinyl aromatic monomer comprises styrene, t-butyl styrene, methyl styrene, a carboxylic acid-functionalized styrene, an amine-functionalized styrene, or a mixture thereof.

5. The electrode of claim 1 wherein the block copolymer has the structure of formula (1).

6. The electrode of claim 1 wherein the block copolymer has the structure of formula (2).

7. The electrode of claim 1 wherein one or more of the high $T_g$ polymers comprise repeat units derived from the group consisting of a vinyl monomer, an aromatic monomer, a methacrylic acid monomer, an acrylic monomer, a siloxane monomer, a cinnamic acid monomer, or a mixture thereof.

8. The electrode of claim 1 wherein one or more of the low $T_g$ polymers comprise repeat units derived from an alkene monomer, an acrylic acid monomer, a methacrylic acid monomer, a vinyl ether monomer, a cyclic ether monomer, an ester monomer, a siloxane monomer, or a mixture thereof.

9. The electrode of claim 8 wherein either:
   one or more of the low $T_g$ polymers comprises repeat units derived from an alkene monomer, the alkene monomer comprising an alpha-olefin, a diene, or a halogenated alkene, or a mixture thereof;
   one or more of the low $T_g$ polymers comprises repeat units derived from an acrylic acid monomer, the acrylic acid monomer comprising an alkyl acrylate, an arylalkyl acrylate, an alkoxyalkyl acrylate, a haloalkyl acrylate, a cyanoalkyl acrylate, or a mixture thereof;
   one or more of the low $T_g$ polymers comprises repeat units derived from a methacrylic acid monomer, the methacrylic acid monomer comprising an alkyl methacrylate, an aminoalkyl methacrylate, or a mixture thereof;

one or more of the low $T_g$ polymers comprises repeat units derived from a vinyl ether acid monomer, the vinyl ether monomer comprising an alkyl vinyl ether;

one or more of the low $T_g$ polymers comprises repeat units derived from a cyclic ether monomer, the cyclic ether monomer comprising tetrahydrofuran, trimethylene oxide, ethylene oxide, propylene oxide, methyl glycidyl ether, butyl glycidyl ether, allyl glycidyl ether, epibromohydrin, epichlorohydrin, 1,2-epoxybutane, 1,2-epoxyoctane, 1,2-epoxydecane, or a mixture thereof;

one or more of the low $T_g$ polymers comprises repeat units derived from an ester monomer, the ester monomer comprising ethylene malonate, vinyl acetate, vinyl propionate, or a mixture thereof;

one or more of the low $T_g$ polymers comprises repeat units derived from a siloxane monomer, the siloxane monomer comprising dimethylsiloxane, diethylsiloxane, methylethylsiloxane, methylphenylsiloxane, or a mixture thereof;

one or more of the low $T_g$ polymers comprises repeat units derived from a cinnamic acid monomer, the cinnamic acid monomer comprising methyl cinnamate, ethyl cinnamate, cinnamic acid, a functionalized derivative of cinnamic acid, or a mixture thereof;

one or more of the low $T_g$ polymers comprises repeat units derived from ethylene, propylene, isopropylene, butylene, isobutylene, t-butylene, butadiene, isoprene, neoprene (polychloroprene), and mixtures thereof; or one or more of the low $T_g$ polymers comprises a fluoroelastomer.

10. The electrode of claim 8 wherein either:

one or more of the low $T_g$ polymers comprises repeat units derived from an alkene monomer, the alkene monomer comprising an alpha-olefin comprising ethylene, propylene, isobutylene, 1-butene, 4-methyl pentene, 1-octene, or a mixture thereof, a diene comprising 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene, or 3-butyl-1,3-octadiene, or a halogenated alkene comprising vinylidene chloride, vinylidene fluoride, hexafluoropropylene, cis-chlorobutadiene, or trans-chlorobutadiene, or a mixture thereof;

one or more of the low $T_g$ polymers comprises repeat units derived from an acrylic acid monomer, the acrylic acid monomer comprising an alkyl acrylate comprising methyl acrylate, ethyl acrylate, propyl acrylate, isopropyl acrylate, butyl acrylate, sec-butyl acrylate, isobutyl acrylate, cyclohexyl acrylate, 2-ethylhexyl acrylate, dodecyl acrylate, hexadecyl acrylate, or a mixture thereof, an arylalkyl acrylate comprising benzyl acrylate, an alkoxyalkyl acrylate comprising 2-ethoxyethyl acrylate or 2-methoxyethyl acrylate, a haloalkyl acrylate comprising 2,2,2-trifluoroethyl acrylate, a cyanoalkyl acrylate comprising 2-cyanoethyl acrylate, or a mixture thereof;

one or more of the low $T_g$ polymers comprises repeat units derived from a methacrylic acid monomer, the methacrylic acid monomer comprising an alkyl methacrylate comprising butyl methacrylate, hexyl methacrylate, 2-ethylhexyl methacrylate, octyl methacrylate, dodecyl methacrylate, hexadecyl methacrylate, octadecyl methacrylate, or a mixture thereof, an aminoalkyl methacrylate comprising diethylaminoethyl methacrylate or 2-tert-butyl-aminoethyl methacrylate, or a mixture thereof;

one or more of the low $T_g$ polymers comprises repeat units derived from a vinyl ether acid monomer, the vinyl ether monomer comprising an alkyl vinyl ether comprising methyl vinyl ether, ethyl vinyl ether, propyl vinyl ether, butyl vinyl ether, isobutyl vinyl ether, 2-ethylhexyl vinyl ether, dodecyl vinyl ether, or a mixture thereof; or one or more of the low $T_g$ polymers comprises a fluoroelastomer comprising repeat units derived from tetrafluoroethylene, hexafluoropropylene, vinylidene fluoride, and mixtures thereof.

11. The electrode of claim 1 wherein the block copolymer is a triblock copolymer having the structure of formula (1) wherein each of the polymers of $R_1$ and $R_3$ has a $T_g$ greater than 70° C., and an average number of repeat units of from about 15 to about 300, and the polymer of $R_2$ has a $T_g$ less than 0° C., and an average number of repeat units of from about 200 to about 5000.

12. The electrode of claim 11 wherein either:

each of the polymers of $R_1$ and $R_3$ comprises polystyrene, polystyrene sulfonate, poly(t-butyl styrene), poly(styrene-r-styrene sulfonate), or a mixture thereof, and each of the polymers of $R_2$ and $R_4$ comprises poly(ethylene), poly(butylene), poly(isobutylene), poly(butadiene), partially sulfonated poly(butadiene), poly(propylene), poly(ethylene-r-propylene), poly(ethylene-r-butylene), poly(ethylene-r-isobutylene), polyisoprene, or a mixture thereof;

each of the polymers of $R_1$ and $R_3$ comprises polystyrene sulfonate and the polymer of $R_2$ comprises polyethylene, poly(isobutylene), poly(butylene), or mixtures thereof;

each of the polymers of $R_1$ and $R_3$ comprises polystyrene and the polymer of $R_2$ comprises partially sulfonated poly(butadiene);

each of the polymers of $R_1$ and $R_3$ comprises poly(t-butyl styrene), each of the polymers of $R_2$ and $R_4$ comprises poly(ethylene-r-propylene), and the polymer of $R_5$ comprises poly(styrene-r-styrene sulfonate);

at least one of the polymers of $R_1$, $R_2$, and $R_3$ comprise repeat units derived from an anionic monomer; or the block copolymer of formula 1 carries an average charge per repeat unit of from about −0.1 to about −0.5.

13. The electrode of claim 11 wherein the block copolymer is a block copolymer having the structure of formula (4) and either:

at least one of the polymers of $R_1$, $R_2$, $R_3$, $R_4$, and $R_6$ comprise repeat units derived from an anionic monomer;

each of the polymers of $R_2$, $R_4$, and $R_6$ comprise repeat units derived from an anionic monomer;

each of the polymers of $R_2$, $R_4$, and $R_6$ has a Young's modulus from about 0.001 GPa to about 2 GPa; or each of the polymers of $R_2$, $R_4$, and $R_6$ has a Young's modulus from about 0.01 GPa to about 0.8 GPa.

14. The electrode of claim 1 wherein the block copolymer is a block copolymer having the structure of formula (2) wherein each of the polymers of $R_1$, $R_3$ and $R_5$ has a $T_g$ greater than 70° C., and an average number of repeat units of from about 15 to about 300, and each of the polymers of $R_2$ and $R_4$ has a $T_g$ less than 0° C., and an average number of repeat units of from about 200 to about 5000.

15. The electrode of claim 14 wherein either:
each of the polymers of $R_1$, $R_3$ and $R_5$ comprises polystyrene, polystyrene sulfonate, poly(t-butyl styrene), poly(styrene-r-styrene sulfonate), or a mixture thereof, and each of the polymers of $R_2$ and $R_4$ comprises poly(ethylene), poly(butylene), poly(isobutylene), poly(butadiene), partially sulfonated poly(butadiene), poly(propylene), poly(ethylene-r-propylene), poly(ethylene-r-butylene), poly(ethylene-r-isobutylene), polyisoprene, or a mixture thereof;
each of the polymers of $R_1$ and $R_3$ comprises polystyrene and the polymer of $R_2$ comprises partially sulfonated poly(butadiene);
each of the polymers of $R_1$ and $R_3$ comprises poly(t-butyl styrene), each of the polymers of $R_2$ and $R_4$ comprises poly(ethylene-r-propylene), and the polymer of $R_5$ comprises poly(styrene-r-styrene sulfonate);
at least one of the polymers of $R_1$, $R_2$, $R_3$, $R_4$, and $R_5$ comprise repeat units derived from an anionic monomer;
each of the polymers of $R_1$, $R_3$ and $R_5$ comprise repeat units derived from an anionic monomer;
the block copolymer of formula 2 carries an average charge per repeat unit of from about −0.1 to about −0.5;
each of the polymers of $R_1$, $R_3$ and $R_5$ has a Young's modulus from about 0.01 GPa to about 50 GPa; or
each of the polymers of $R_1$, $R_3$ and $R_5$ has a Young's modulus from about 0.5 GPa to about 5 GPa.

16. The electrode of claim 1 wherein the polyanionic counterion component further comprises a random copolymer, wherein the random copolymer comprises:
(a) styrenic repeat units comprising styrene, t-butyl styrene, t-butyl styrene, methyl styrene, a carboxylic acid-functionalized styrene, an amine-functionalized styrene, or a mixture thereof; and
(b) elastomeric repeat units comprising polyethylene, polybutylene, polybutadiene, polyisopropene, polyisobutylene, or a mixture thereof;
wherein from about 10 to 100 mol % of the repeat units are functionalized with a negatively charged functional group, based on the number of styrenic repeat units.

17. The electrode of claim 1 wherein the conductive monomer or the conductive polymer is cationic.

18. The electrode of claim 1 wherein the conductive polymer comprises a polyacetylene, a poly(vinyl alcohol), a poly(fluorene), a polyphenylene, a polyphenylene vinylene, a polypyrene, a polyazulene, a polynaphthalene, a poly(pyrrole), a polycarbazole, a polyindole, a polyazepine, a polyaniline, a polyacene, a polythiophene, a polythiophene vinylene, a poly(p-phenylene sulfide), a polypyridine, or a precursor or blend thereof.

19. The electrode of claim 1 wherein the conductive monomer comprises acetylene, fluorene, para-phenylene, pyrene, pyrrole, carbazole, indole, phenyl azide, aniline, thiophene, pyridine, or a mixture or functionalized derivative thereof.

20. The electrode of claim 1 wherein the conductive monomer comprises a mixture of EDOT and a functionalized EDOT derivative.

21. The electrode of claim 1 wherein the polymerization mixture further comprises a crosslinking component.

22. The electrode of claim 21 wherein the crosslinking component comprises a monomer functionalized with a group selected from a silane, an acrylate, a derivative thereof, or a combination thereof.

23. The electrode of claim 1 wherein the polymerization mixture further comprises a surfactant component comprising one or more surfactants.

24. The electrode of claim 1 wherein the block copolymer has the structure of formula (1) or (2).

25. The electrode of claim 1 wherein the negatively charged functional group comprises a phosphate group, a phosphonate group, a sulfamate group, a carboxylate group, a sulfate group, a sulfonate group, or a combination thereof.

26. The electrode of claim 25 wherein the negatively charged functional group comprises a sulfonate group, and the sulfonate group comprises a sodium counterion.

27. The electrode of claim 1 wherein either:
one or more of the high Tg polymers comprises repeat units derived from a vinyl aromatic monomer, the vinyl aromatic monomer comprising an unsubstituted vinyl aromatic, a vinyl substituted aromatic, a ring-substituted vinyl aromatic, a ring-alkoxylated vinyl aromatic, a ring-halogenated vinyl aromatic, a ring-ester-substituted vinyl aromatic, a ring-amino-substituted vinyl aromatic, a ring-silyl-substituted aromatic, a vinyl pyridine, vinyl carbazole, vinyl ferrocene, or a mixture thereof;
one or more of the high Tg polymers comprises repeat units derived from a vinyl monomer, the vinyl monomer comprising a vinyl ester, a vinyl amine, a vinyl halide, an alkyl vinyl ether, vinyl pyrrolidone, or a mixture thereof;
one or more of the high Tg polymers comprises repeat units derived from an aromatic monomer, the aromatic monomer comprising acenaphthalene, indene, or a mixture thereof;
one or more of the high Tg polymers comprises repeat units derived from a methacrylic acid monomer, the methacrylic acid monomer comprising a methacrylic acid anhydride, a methacrylic acid ester, isobornyl methacrylate, trimethylsilyl methacrylate, methacrylonitrile, or a mixture thereof;
one or more of the high Tg polymers comprises repeat units derived from a methacrylic acid ester monomer, the methacrylic acid ester monomer comprising an alkyl methacrylate, an aromatic methacrylate, an hydroxyalkyl methacrylate, or a mixture thereof;
one or more of the high Tg polymers comprises repeat units derived from an acrylic monomer, the acrylic monomer comprising an acrylic acid ester, acrylonitrile, or mixtures thereof;
one or more of the high Tg polymers comprises repeat units derived from a siloxane monomer; or
the high Tg polymer comprises styrene.

28. The electrode of claim 27 wherein either:
one or more of the high Tg polymers comprises repeat units derived from an unsubstituted vinyl aromatic comprising styrene or 2-vinyl naphthalene, a vinyl substituted aromatic comprising alpha-methyl styrene, a ring-substituted vinyl aromatic comprising 3-methyl styrene, 4-methyl styrene, 2,4-dimethyl styrene, 2,5-dimethyl styrene, 3,5-dimethyl styrene, 2,4,6-trimethylstyrene, 4-tert-butylstyrene, or a mixture thereof, a ring-alkoxylated vinyl aromatic comprising 4-methoxystyrene or 4-ethoxystyrene, a ring-halogenated vinyl aromatic comprising 2-chlorostyrene, 3-chlorostyrene, 4-chlorostyrene, 2,6-dichlorostyrene, 4-bromostyrene, 4-fluorostyrene, or a mixture thereof, a ring-ester-substituted vinyl aromatic comprising 4-acetoxystyrene, a ring-hydroxylated vinyl aromatic comprising 4-hydroxystyrene, a ring-amino-substituted vinyl aromatic comprising 4-amino styrene, a ring-silyl-substituted aromatic comprising p-dimethylethoxy siloxy styrene, a vinyl pyridine comprising 2-vinyl pyridine or 4-vinyl pyridine or a mixture thereof;

one or more of the high Tg polymers comprises repeat units derived from a vinyl monomer, the vinyl monomer comprising a vinyl ester comprising vinyl benzoate, vinyl 4-tert-butyl benzoate, vinyl cyclohexanoate, vinyl pivalate, vinyl trifluoroacetate, or vinyl butyral, a vinyl halide comprising vinyl chloride or vinyl fluoride, an alkyl vinyl ether comprising tert-butyl vinyl ether or cyclohexyl vinyl ether, or a mixture thereof;

one or more of the high Tg polymers comprises repeat units derived from a methacrylic acid ester monomer, the methacrylic acid ester monomer comprising an alkyl methacrylate comprising methyl methacrylate, ethyl methacrylate, isopropyl methacrylate, isobutyl methacrylate, t-butyl methacrylate, or cyclohexyl methacrylate, an aromatic methacrylate comprising phenyl methacrylate, an aromatic alkyl methacrylate comprising benzyl methacrylate, an hydroxyalkyl methacrylate comprising 2-hydroxyethyl methacrylate or 2-hydroxypropyl methacrylate, or a mixture thereof;

one or more of the high Tg polymers comprises repeat units derived from an acrylic monomer, the acrylic monomer comprising an acrylic acid ester comprising tert-butyl acrylate, hexyl acrylate, or isobornyl acrylate, or mixtures thereof; or one or more of the high Tg polymers comprises repeat units derived from a siloxane monomer comprising diphenylsiloxane.

29. The electrode of claim 1 wherein either:

the conductive polymer comprises a polythiophene, the polythiophene selected from poly(3,4-ethylenedioxythiophene) or a functionalized derivative thereof;

the conductive polymer is derived from a functionalized derivative of 3,4-ethylenedioxythiophene (EDOT) selected from the group consisting of hydroxymethyl-EDOT, EDOT-vinyl, EDOT-ether allyl, EDOT-acrylate, or a combination thereof;

the conductive polymer comprises a polythiophene, the polythiophene selected from poly(hexylthiophene) or a salt or functionalized derivative thereof;

the conductive polymer comprises poly-4-vinylpyridine;

the conductive polymer comprises poly(diallyldimethylammonium chloride);

the conductive monomer comprises 3,4-ethylenedioxythiophene;

the conductive monomer comprises a functionalized derivative of 3,4-ethylenedioxythiophene (EDOT) selected from the group consisting of hydroxymethyl-EDOT, EDOT-vinyl, EDOT-ether allyl, EDOT-COOH, EDOT-MeOH, EDOT-silane, EDOT-vinyl, EDOT-acrylate, EDOT-sulfonate, EDOT-amine, EDOT-amide, and combinations thereof;

the conductive monomer comprises a functionalized derivative of 3,4-ethylenedioxythiophene (EDOT) comprising an alkene functional group;

the conductive monomer comprises hexylthiophene or a functionalized derivative thereof;

the conductive monomer comprises 4-vinylpyridine; or the conductive monomer comprises 3-methyl thiophene.

30. A coated electrode comprising an electrically conductive substrate and a polymeric coating, wherein the polymeric coating comprises a reaction product of a polymerization mixture comprising:

a conductive monomer or a conductive polymer; and a polyanionic counterion component comprising a random copolymer, wherein the random copolymer comprises:

(a) styrenic repeat units comprising styrene, t-butyl styrene, methyl styrene, a carboxylic acid-functionalized styrene, an amine-functionalized styrene, or a mixture thereof; and (b) elastomeric repeat units comprising polyethylene, polybutylene, polybutadiene, polyisopropene, polyisobutylene, or a mixture thereof;

wherein from about 10 to 100 mol % of the repeat units are functionalized with a negatively charged functional group comprising a phosphate group, a phosphonate group, a sulfamate group, a carboxylate group, a sulfate group, a sulfonate group, or a combination thereof; and wherein the polymerization mixture further comprises a secondary counterion component, and either:

the secondary counterion component comprises polystyrene sulfonate or a block copolymer derived from polystyrene sulfonate and maleic anhydride (PSS-CoMA), and the polyanionic counterion component comprises sulfonated polystyrene-block-poly(ethylene-r-butylene)-block-polystyrene (SPSEBS), polystyrene-block-polyisobutylene-block-polystyrene (SPSIBS), or sulfonated polystyrene-r-ethylene (SPSE);

the secondary counterion component comprises a random copolymer comprising:

(a) styrenic repeat units comprising styrene, t-butyl styrene, methyl styrene, a carboxylic acid-functionalized styrene, an amine-functionalized styrene, or a mixture thereof; and (b) elastomeric repeat units comprising polyethylene, polybutylene, polybutadiene, polyisopropene, polyisobutylene, or a mixture thereof; wherein from about 10 to 100 mol % of the repeat units of the random copolymer are functionalized with the negatively charged functional group; or the secondary counterion component comprises carbon nanotubes functionalized with the negatively charged functional group, and either: the negatively charged functional group comprises a phosphate group, a phosphonate group, a carboxylate group, a sulfate group, a sulfonate group, or a combination thereof; the negatively charged functional group comprises polyaminobenzene sulfonate; or the polyanionic counterion component comprises functionalized carbon nanotubes in combination with one or more additional polyanionic species.

31. The electrode of claim 30 wherein the secondary counterion component comprises polystyrene sulfonate or a block copolymer derived from polystyrene sulfonate and maleic anhydride (PSS-CoMA), and the polyanionic counterion component comprises sulfonated polystyrene-block-poly(ethylene-r-butylene)-block-polystyrene (SPSEBS), polystyrene-block-polyisobutylene-block-polystyrene (SPSIBS), or sulfonated polystyrene-r-ethylene (SPSE).

32. The electrode of claim 30 wherein the secondary counterion component comprises a random copolymer comprising:

(a) styrenic repeat units comprising styrene, t-butyl styrene, methyl styrene, a carboxylic acid-functionalized styrene, an amine-functionalized styrene, or a mixture thereof; and (b) elastomeric repeat units comprising polyethylene, polybutylene, polybutadiene, polyisopropene, polyisobutylene, or a mixture thereof;

wherein from about 10 to 100 mol % of the repeat units of the random copolymer of the secondary counterion component are functionalized with a negatively charged functional group.

33. The electrode of claim 30 wherein the secondary counterion component comprises carbon nanotubes functionalized with a negatively charged functional group, and either:
- the negatively charged functional group comprises a phosphate group, a phosphonate group, a carboxylate group, a sulfate group, a sulfonate group, or a combination thereof;
- the negatively charged functional group comprises polyaminobenzene sulfonate; or
- the polyanionic counterion component comprises functionalized carbon nanotubes in combination with one or more additional polyanionic species.

34. A medical device comprising the coated electrode of claim 1.

35. The medical device of claim 34, wherein the medical device is implantable.

* * * * *